US012778906B2

(12) United States Patent
Kwon et al.

(10) Patent No.: US 12,778,906 B2
(45) Date of Patent: Nov. 3, 2026

(54) PHARMACEUTICAL COMPOSITION FOR PREVENTING OR TREATING MUSCULAR WEAKNESS-RELATED DISEASES COMPRISING ALVERINE, 4-HYDROXY ALVERINE, DERIVATIVE THEREOF, OR PHARMACEUTICALLY ACCEPTABLE SALT THEREOF

(71) Applicant: AVENTI INC., Daejeon (KR)

(72) Inventors: Ki-Sun Kwon, Daejeon (KR); Younglang Lee, Daejeon (KR); Jong Hyun Yoon, Daejeon (KR); Seung-Min Lee, Daejeon (KR); Chang Hoon Jeon, Daejeon (KR); Tai Hwan Ha, Daejeon (KR); Do Yeun Jeong, Daejeon (KR)

(73) Assignee: AVENTI INC., Daejeon (KR)

( * ) Notice: Subject to any disclaimer, the term of this patent is extended or adjusted under 35 U.S.C. 154(b) by 775 days.

(21) Appl. No.: 17/917,658

(22) PCT Filed: Apr. 9, 2021

(86) PCT No.: PCT/KR2021/004523

§ 371 (c)(1),
(2) Date: Oct. 7, 2022

(87) PCT Pub. No.: WO2021/206513

PCT Pub. Date: Oct. 14, 2021

(65) Prior Publication Data

US 2023/0149326 A1 May 18, 2023

(30) Foreign Application Priority Data

Apr. 9, 2020 (KR) ........................ 10-2020-0043481
Nov. 25, 2020 (KR) ........................ 10-2020-0160258

(51) Int. Cl.
*A61K 31/135* (2006.01)
*A61K 9/00* (2006.01)
*A61P 21/00* (2006.01)

(52) U.S. Cl.
CPC .......... *A61K 31/135* (2013.01); *A61K 9/0056* (2013.01); *A61P 21/00* (2018.01)

(58) Field of Classification Search
None
See application file for complete search history.

(56) References Cited

U.S. PATENT DOCUMENTS

2013/0023488 A1 1/2013 Wu
2021/0038595 A1 2/2021 Xie et al.

FOREIGN PATENT DOCUMENTS

CN 108057032 A 5/2018
JP 6-500094 A 1/1994
JP 2012-111718 A 6/2012
KR 10-2014-0028653 A 3/2014
KR 10-2186564 B1 12/2020
WO 92/02488 A1 2/1992
WO 2008/133884 A2 11/2008
WO 2016/156396 A1 10/2016

OTHER PUBLICATIONS

Ju et al., International Journal of Molecular Medicine (2009), 23(2), pp. 205-209.*
Hara et al. Chemical and Pharmaceutical Bulletin (1972), 20(5), pp. 1063-1067.*
Kulz et al., Berichte der Deutschen Chemischen Gesellschaft (1939), 72B, pp. 2161-2167 (English language CAS SciFinder abstract).*
Kulz et al., Berichte der Deutschen Chemischen Gesellschaft (1939), 72B, pp. 2161-2167.*
Registry (STN) [online], 2008 (retrieval date Jan. 9, 2025), CAS registry No. 1026980-33-5.
Registry (STN) [online], 2005 (retrieval date Jan. 15, 2025), CAS registry No. 807264-08-0.
Registry (STN) [online], 1999 (retrieved date Jan. 15, 2025), CAS registry No. 246178-12-1.
Guangrong Zheng, et al., "Defunctionalized Lobeline Analogues: Structure-Activity of Novel Ligands for the Vesicular Monoamine Transporter", J Med Chem, Aug. 25, 2005, vol. 48, No. 17, pp. 5551-5560 (22 pages).
Anita Annaházi et al., "Role of antispasmodics in the treatment of irritable bowel syndrome", World J Gastroenterol, May 28, 2014 pp. 6031-6043, vol. 20, No. 20.
Chemical Abstract Compound. STNext Cas No. 246178-12-1 (Nov. 4, 1999). See the chemical formulas.
Chemical Abstract Compound. STNext Cas No. 807264-08-0 (Jan. 2, 2005). See the chemical formulas.
M Hayase et al., "Evolving mechanisms of action of alverine citrate on phasic smooth muscles", British Journal of Pharmacology, 2007, pp. 1228-1238, vol. 152.
Anne-Marie Coelho et al., "Rectal antinociceptive properties of alverine citrate are linked to antagonism at the 5-HT1A receptor subtype", Journal of Pharmacy and Pharmacology, 2001, pp. 1419-1426, vol. 53.
Ju Yeon Kwak et al., "Pharmacological Interventions for Treatment of Sarcopenia: Current Status of Drug Development for Sarcopenia", Ann Geriatr Med Res, 2019, pp. 98-104, vol. 23, vol. 3.

(Continued)

*Primary Examiner* — Brian J Davis
(74) *Attorney, Agent, or Firm* — Sughrue Mion, PLLC

(57) ABSTRACT

A pharmaceutical or food composition including alverine, 4-hydroxy alverine, a derivative thereof, or a salt thereof and their uses are disclosed. The composition is useful for preventing, alleviating, or treating muscular weakness-related diseases. When myoblasts are treated with the alverine, 4-hydroxy alverine, derivative thereof, or salt thereof, differentiation into myotubes is promoted. Therefore, the alverine, 4-hydroxy alverine, derivative thereof, or salt thereof can be effectively used in the promotion of differentiation of myoblasts and the prevention, alleviation, or treatment of muscular weakness-related diseases.

8 Claims, 10 Drawing Sheets

(56) References Cited

OTHER PUBLICATIONS

Jiayu Yin et al., "New insights into the pathogenesis and treatment of sarcopenia in chronic heart failure", Theranostics, 2019, pp. 4019-4029, vol. 9, Issue 14.
Alfonso J. Cruz-Jentoft et al., "Sarcopenia: revised European consensus on definition and diagnosis", Age and Ageing, 2019, pp. 16-31, vol. 48.
Jessica Hiu-Tung Lo et al., "Sarcopenia: Current treatments and new regenerative therapeutic approaches", Journal of Orthopaedic Translation, 2020, pp. 38-52, vol. 23.
Bruce M. Carlson et al., "Skeletal Muscle Regeneration in Very Old Rats", Journal of Gerontology: Biological Sciences, 2001, pp. B224-B233, vol. 56A, No. 5.
Luc A Sabourin et al., "The molecular regulation of myogenesis", Clin Genet, 2000, pp. 16-25, vol. 57.
Francesca Riuzzi et al., "Cellular and molecular mechanisms of sarcopenia: the S100B perspective", Journal of Cachexia, Sarcopenia and Muscle, 2018, pp. 1255-1268, vol. 9.
Mary F. O'Leary et al., "IL-15 promotes human myogenesis and mitigates the detrimental effects of TNFα on myotube development", Science Reports, Oct. 11, 2017, pp. 1-11, vol. 7, No. 12997.
International Search Report of PCT/KR2021/004523 dated Jul. 21, 2021 [PCT/ISA/210].
Elena Guerrieri et al., "Structural determinants of diphenethylamines for interaction with the k opioid receptor: Synthesis, pharmacology and molecular modeling studies," Bioorganic & Medicinal Chemistry Letters, 2016, vol. 26, No. 19, pp. 4769-4774 (6 pages total).
Fang Zheng et al., "Computational neural network analysis of the affinity of lobeline and tetrabenazine analogs for the vesicular monoamine transporter-2," Bioorganic & Medicinal Chemistry, 2007, vol. 15, pp. 2975-2992 (18 pages total), XP-002515369.
F. F. Blicke et al., "Antispasmodics. IV," J. Am. Chem. Soc., 1939, vol. 61, No. 4, pp. 774-776 (3 pages total).
Amelia D. Dunn et al., "Signaling Properties of Structurally Diverse Kappa Opioid Receptor Ligands: Toward in Vitro Models of in Vivo Responses," ACS Chemical Neuroscience, 2019, vol. 10, No. 8, pp. 3590-3600 (11 pages total).
Jong Hyeon Yoon et al., "Alverine citrate promotes myogenic differentiation and ameliorates muscle atrophy," Biochemical and Biophysical Research Communications, 2022, vol. 586, pp. 157-162 (6 pages total).
Extended European Search Report issued Apr. 18, 2024 in Application No. 21785575.8.
Communication issued Aug. 31, 2024 in Chinese Patent Application No. 202180026737.9.
Fritz Kulz et al., "Berichte der Deutschen Chemischen Gesellschaft [Abteilung] B: Abhandlungen", Aus d. Pharmazeut. u. d. Pharmakolog. Institut d. Universit at Kiel., 1939, 72B, pp. 2161-2167 (7 pages total).
Chemical Abstract Compound STN on the Web Registry Chemical Abstract RN 2378650-30-5, Nov. 5, 2019, (215 pages).

* cited by examiner

[Fig. 1]
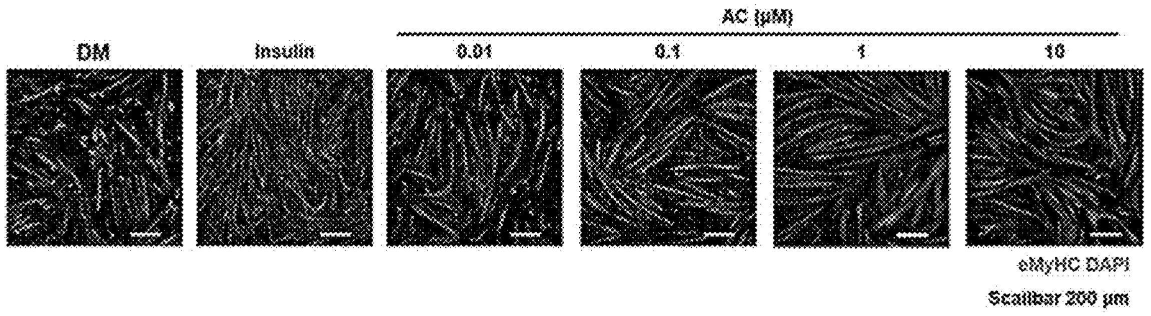
[Fig. 2]
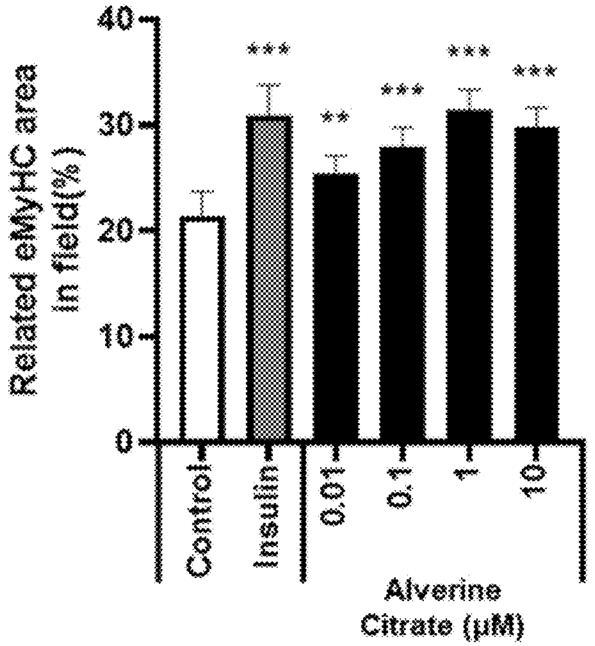

[Fig. 3]
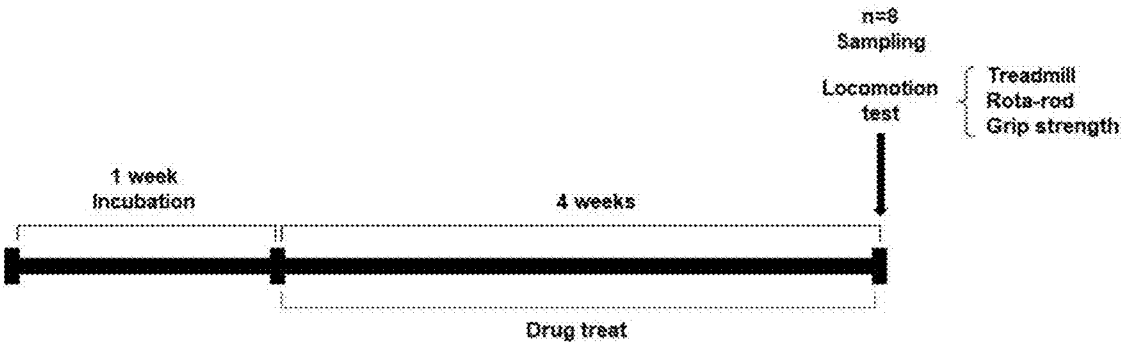
[Fig. 4]
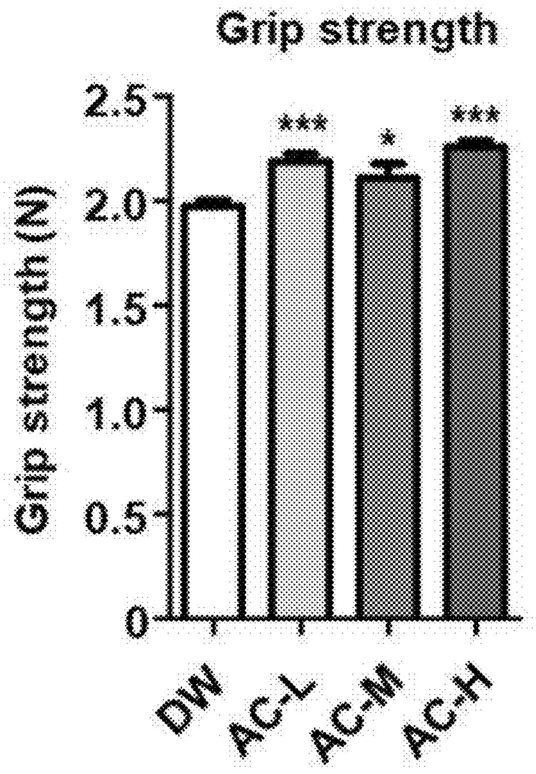

[Fig. 5]
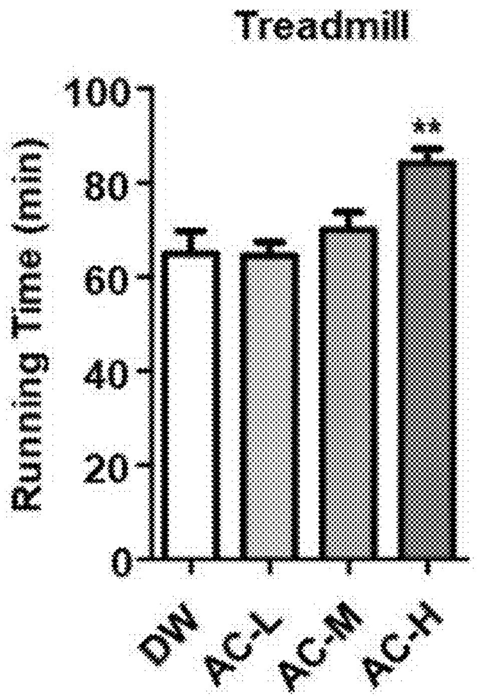
[Fig. 6]
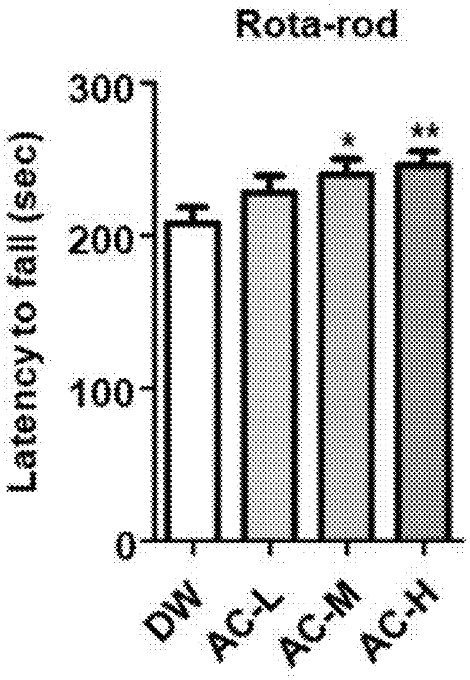

[Fig. 7]
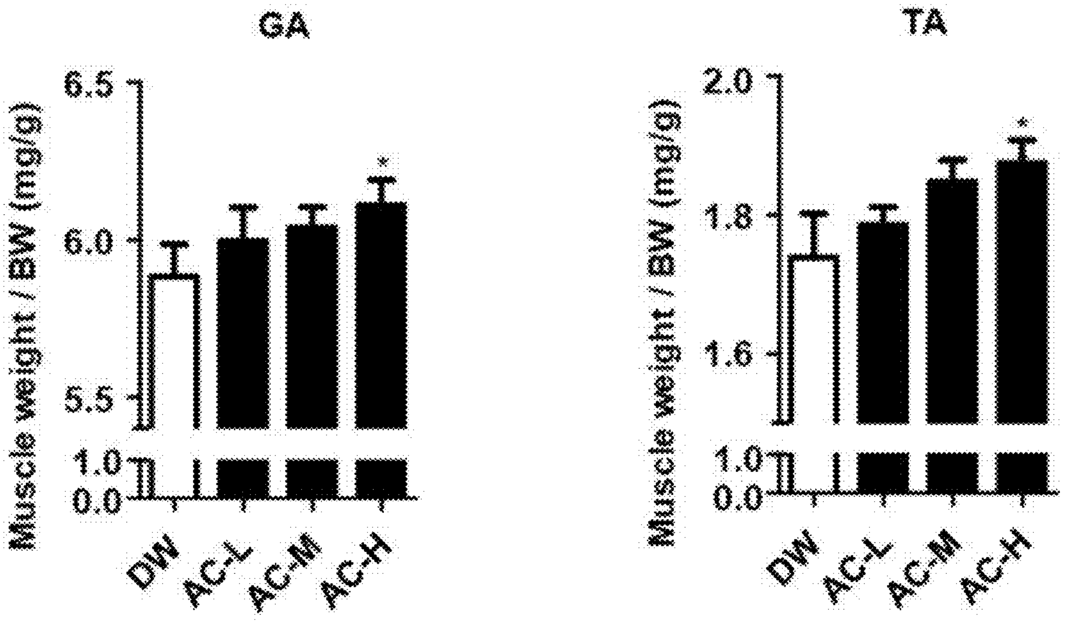
[Fig. 8]
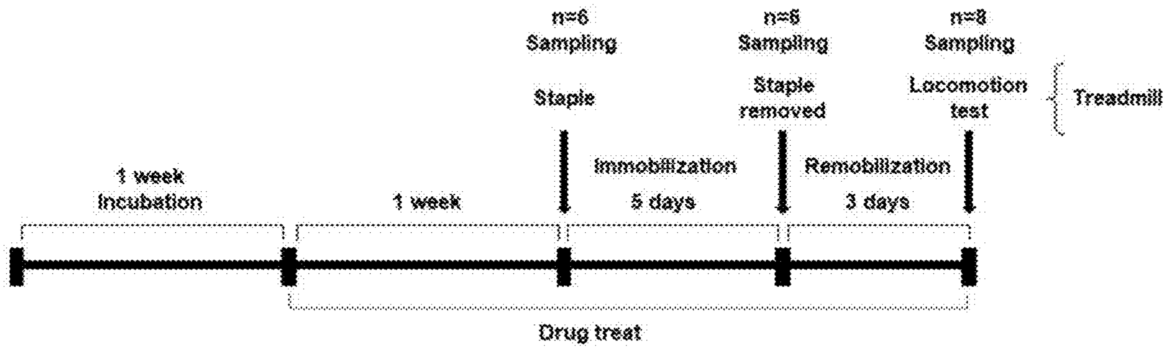

[Fig. 9]
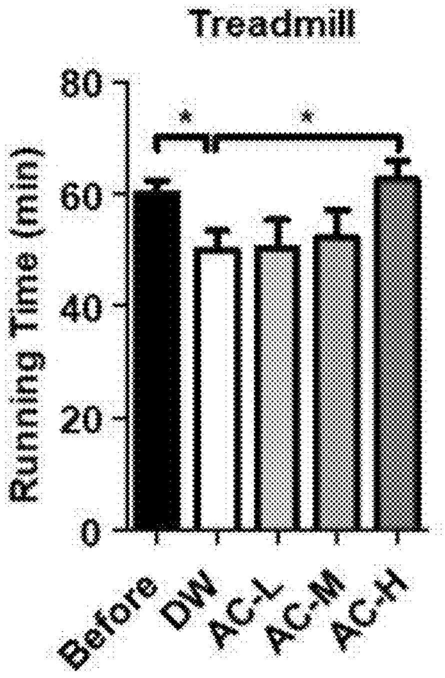
[Fig. 10]
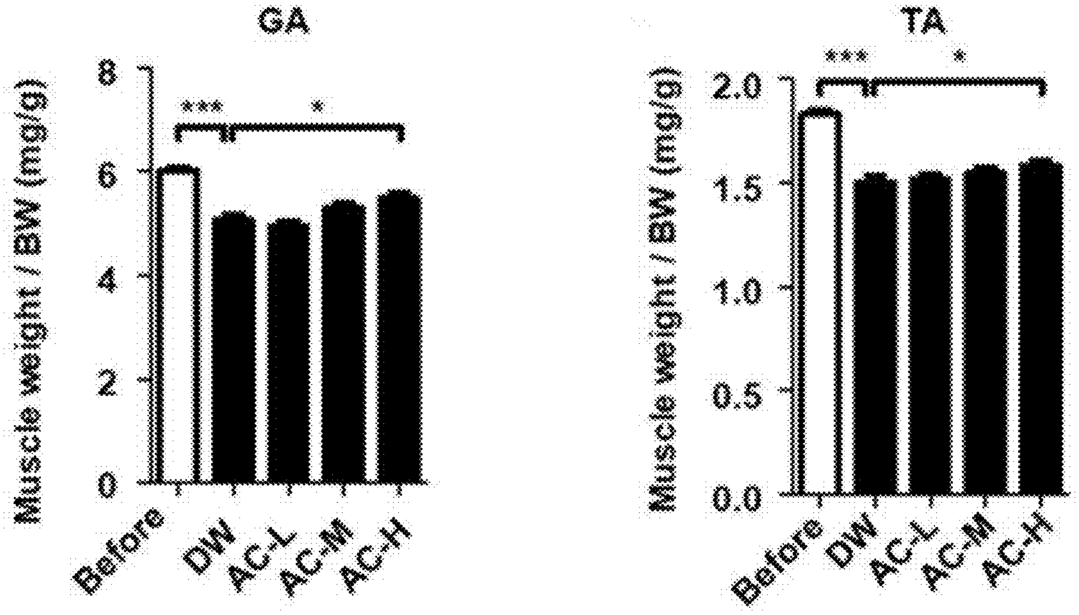

[Fig. 11]
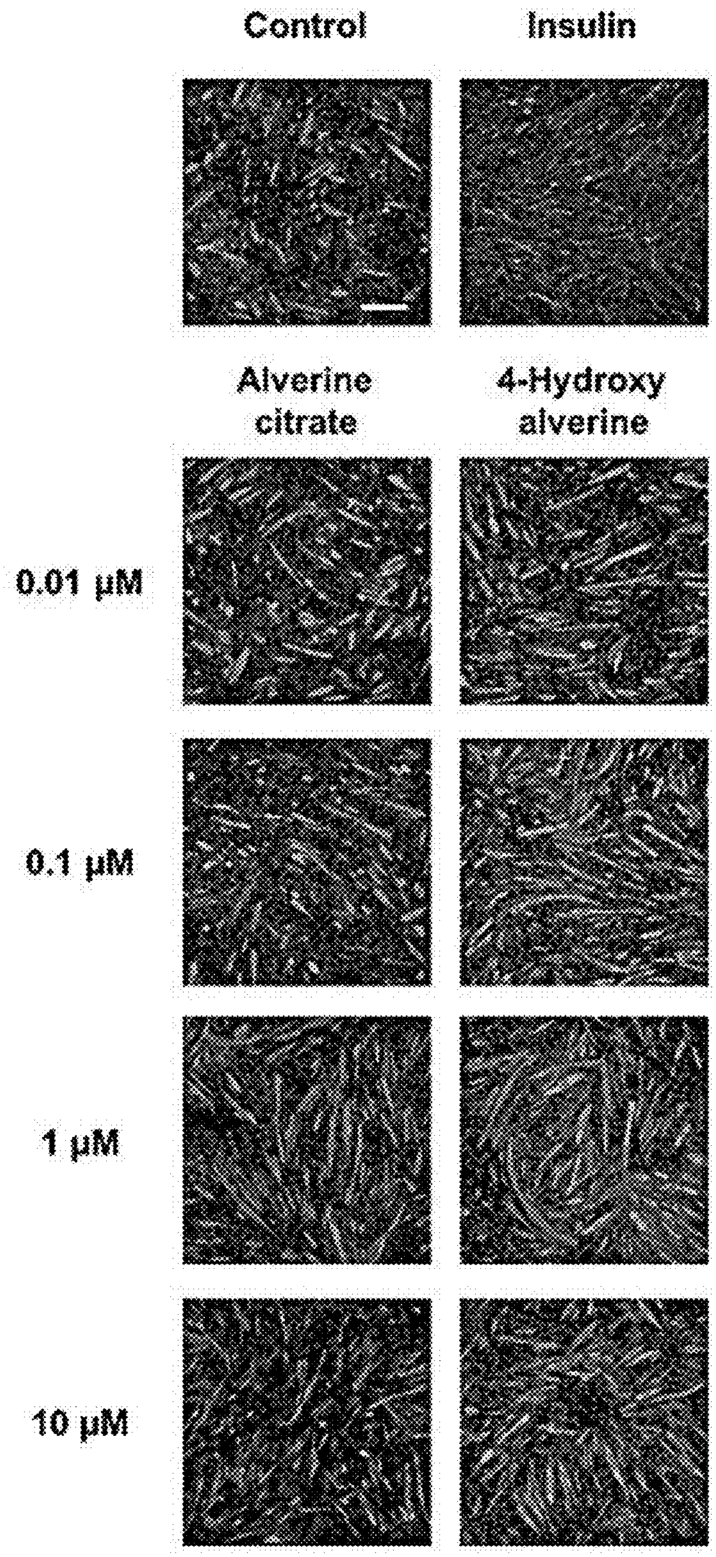

[Fig. 12]
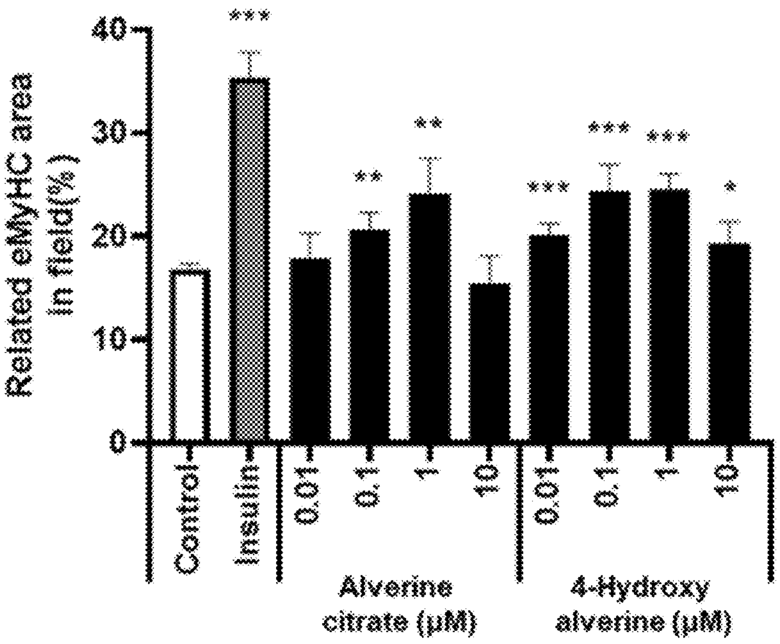
[Fig. 13]
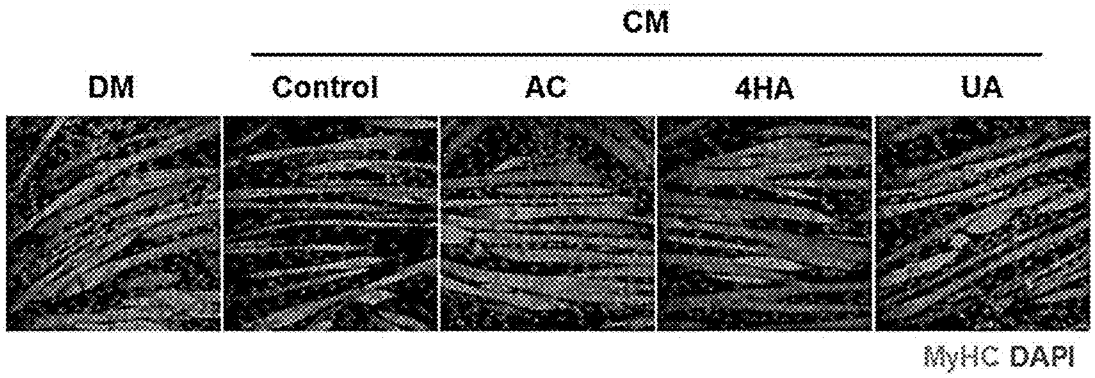

[Fig. 14]
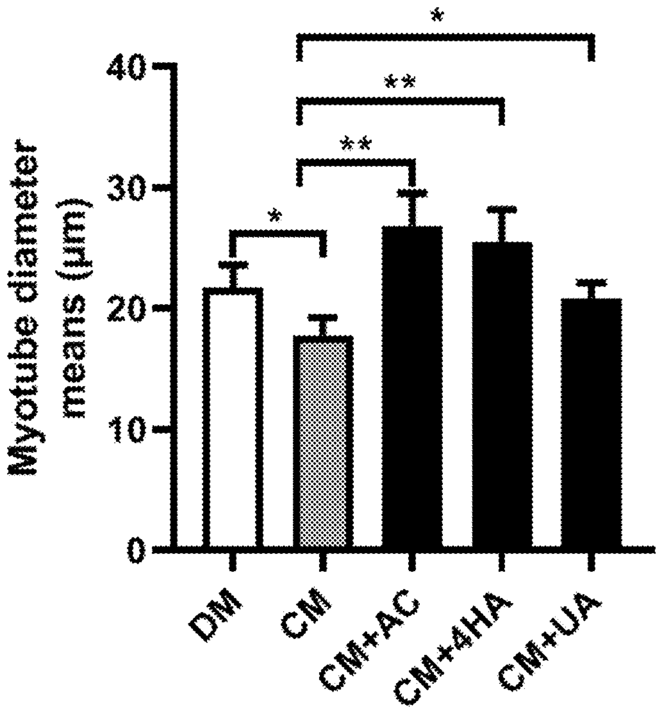

[Fig. 15]
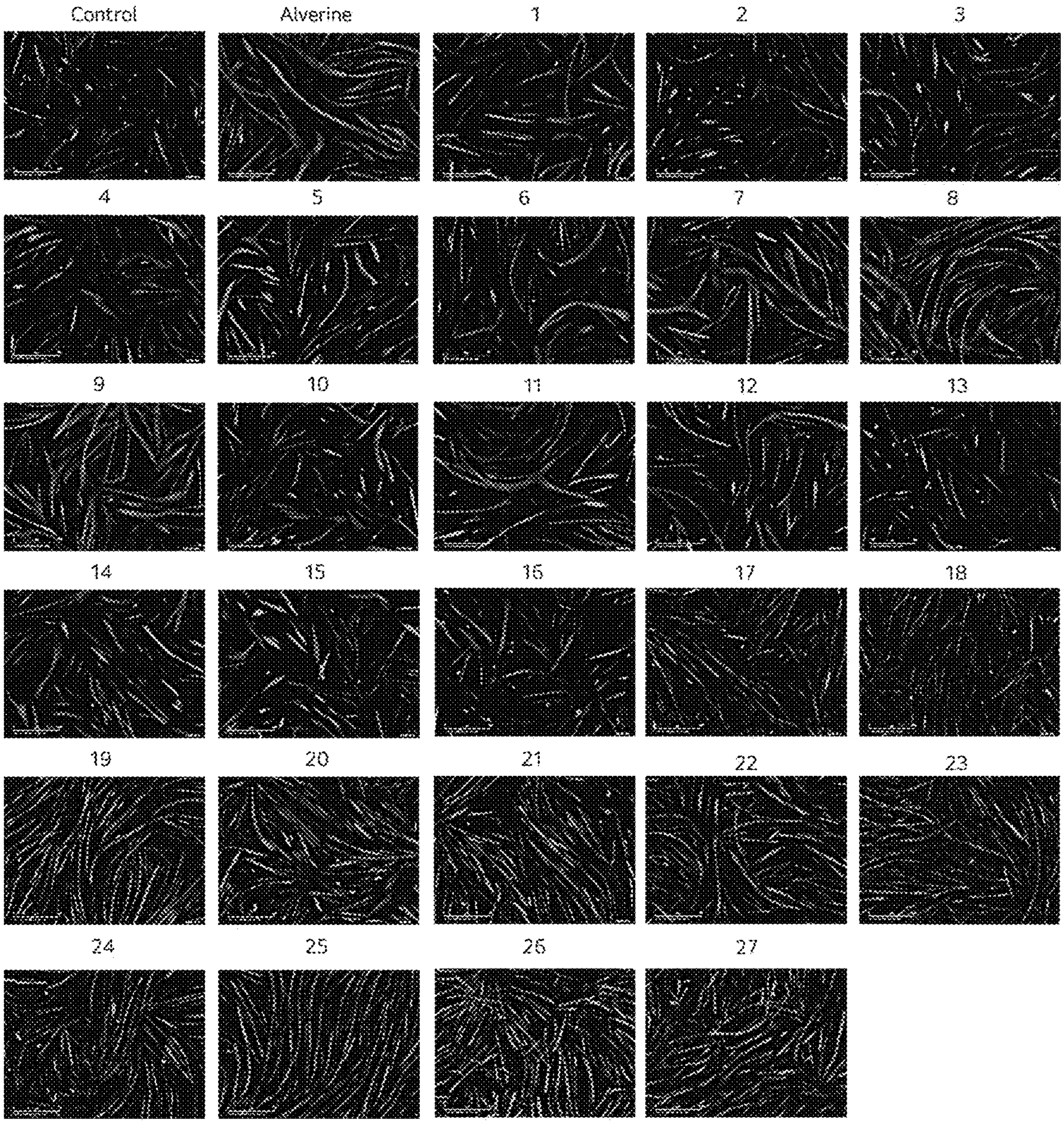

[Fig. 16]
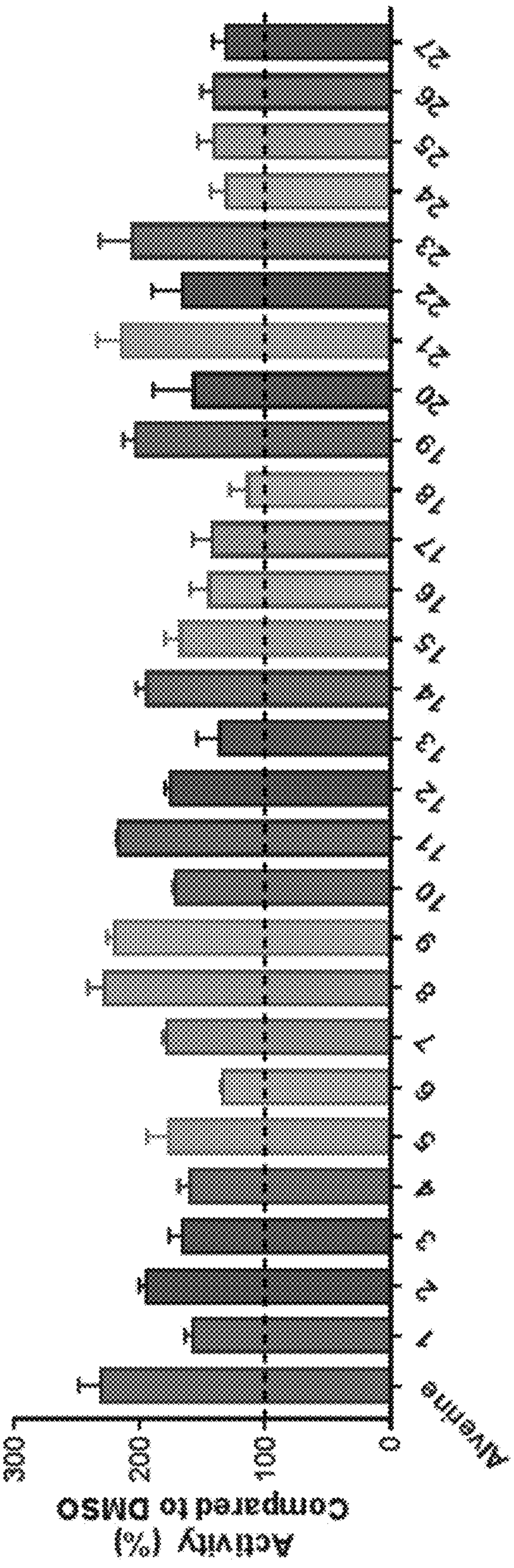

PHARMACEUTICAL COMPOSITION FOR PREVENTING OR TREATING MUSCULAR WEAKNESS-RELATED DISEASES COMPRISING ALVERINE, 4-HYDROXY ALVERINE, DERIVATIVE THEREOF, OR PHARMACEUTICALLY ACCEPTABLE SALT THEREOF

CROSS REFERENCE TO RELATED APPLICATIONS

This application is a National Stage of International Application No. PCT/KR2021/004523, filed Apr. 9, 2021, claiming priorities to Korean Patent Application No. 10-2020-0043481, filed Apr. 9, 2020 and Korean Patent Application No. 10-2020-0160258, filed Nov. 25, 2020.

TECHNICAL FIELD

The present invention relates to a pharmaceutical composition for preventing or treating muscle weakness-related condition, comprising alverine, 4-hydroxy alverine, a derivative thereof, or a pharmaceutically acceptable salt thereof.

BACKGROUND ART

Diseases associated with weakening of muscle strength include sarcopenia, which progresses with age, and muscular dystrophy, which is a degenerative myopathy associated with necrosis of muscle fibers due to genetic mutations.

Sarcopenia involves a gradual decline in muscle strength due to age-related loss of muscle mass. Sarcopenia is accompanied not only by a decline in muscle mass, but also by changes in the types of muscle fibers. Sarcopenia causes various signs of aging and functional impairments seen in old age. Muscular dystrophy is caused by deletions or mutations in muscle-related genes and induces necrosis and degeneration in muscle fibers, which leads to disability or death. Cachexia is a condition characterized by weakening of muscle strength, frequently found in cancer patients. Often observed in cancer patients are loss of muscle mass and loss of muscle strength due to excessive skeletal muscle catabolism from increased metabolism. Since such disturbed metabolism eventually reaches a stage where recovery cannot be made even with food intake, more active treatments such as drug treatment are necessary.

Since sarcopenia treatment drugs currently in development reportedly have shown extremely limited efficacy in clinical trials, it is considered that there are no definitive drug candidates for sarcopenia at present (Ju Yeon Kwak, Ki-Sun Kwon, *Ann Geriatr Med Res.* 98-104, 2019). Thus, presently, only supplementary treatment regimen through physical exercise and nutritional intake are the only method that is safe and produces definitive positive results. Physical exercise may have beneficial influence on skeletal muscles through various mechanisms such as mTORC1 activation, oxidative stress reduction, inflammation reduction, increased mitochondrial production, and the like (Jiayu Yin et al., *Theranostics,* 4019-4029, 2019). Physical exercise and nutritional intake do produce improvements in terms of muscle strength, muscle functions, and muscle mass, but are limited in their efficacy and are difficult to benefit the elderly who cannot exercise due to physical disability or have low nutrient absorption.

However, sarcopenia is a multifactorial disease with various causes, and since there are large differences in muscles mass between race, age, and sex, etc., there are no consistent diagnostic standards for sarcopenia. In 2019, EWGSOP further classified sarcopenia into the following three groups based on muscle mass, muscle strength, and physical performance: probable-sarcopenia, confirmed sarcopenia, severe sarcopenia (AJ Cruz-Jentoft et al., *Age Ageing,* 601, 2019). Though the molecular biological mechanism underlying sarcopenia is not clearly understood, mitochondrial fusion/fission failures, oxidative stress, inflammations, and stem cell depletion, etc. are considered to be the causes of sarcopenia (Jessica Hiu-tung Lo et al., *J Orthop Translat,* 38-52, 2020).

Satellite cells are stem cells found in adult muscles and are necessary in regeneration of damaged skeletal muscles. In mice, the number of satellite cells in muscles was found to decrease with aging. In human, decrease in satellite cells is observed in type II muscles. Such decreasing number of satellite cells may contribute to the development of sarcopenia and is related to muscle regeneration failures in aged animals (Carlson et al., *J Gerontol*, B224-233, 2001).

So far, research on skeletal muscle hypertrophy and regeneration capability have been focusing on regulation of differentiation of myoblasts by myogenic regulatory factors (MRFs) such as MyoD, Mef2, and myogenin (Sabourin L A and Rudnicki M A., *Clin Genet.* 2000 January; 57(1):16-25.). Since improving differentiation capability and regeneration capability of myoblasts by drug therapy causes muscle hypertrophy or improve muscle functions, there have been many attempts made to exploit such approach to resolve age-induced decline in muscle functions (Francesca Riuzzi et al., *J Cachexia Sarcopenia Muscle,* 1255-1268, 2018; Mary F. O'Leary, *Sci Rep.* 12997, 2017; Jin-A Kim and Seong Min Kim, *BMC Complement Altern Med,* 287, 2019). That is, improving the function of satellite cells and increasing the pool of satellite cells may be a strategy to suppress the development of sarcopenia and improve the capacity for muscle regeneration. Accordingly, there is a need to develop a substance which can promote the differentiation of myoblasts.

PRIOR ART DOCUMENTS

Non-Patent Documents (Non-Patent Document 1) Ju Yeon Kwak, Ki-Sun Kwon, *Ann Geriatr Med Res.* 98-104, 2019

(Non-Patent Document 2) Jiayu Yin, Xiang Lu, Zhiyuan Qian, Weiting Xu and Xiang Zhou, *Theranostics,* 4019-4029, 2019

(Non-Patent Document 3) AJ Cruz-Jentoft et al., *Age Ageing,* 601, 2019

(Non-Patent Document 4) Jessica Hiu-tung Lo, Kin PongU, TszlamYiu, *J Orthop Translat,* 38-52, 2020

(Non-Patent Document 5) Carlson et al., *J Gerontol*, B224-233, 2001

(Non-Patent Document 6) Sabourin L A, Rudnicki M A., *Clin Genet.* 2000 January; 57(1):16-25.

(Non-Patent Document 7) Francesca Riuzzi, Guglielmo Sorci, Cataldo Arcuri, *J Cachexia Sarcopenia Muscle,* 1255-1268, 2018, (Non-Patent Document 8) Mary F. O'Leary, *Sci Rep.* 12997, 2017, (Non-Patent Document 9) Jin-A Kim, Seong Min Kim, *BMC Complement Altern Med,* 287, 2019

DISCLOSURE OF INVENTION

Technical Problem

The present inventors have endeavored to develop a substance that can promote differentiation of myoblasts to thereby increase muscle mass and effectively restore muscle functions. As a result, the present inventors have found that alverine, 4-hydroxy alverine, a derivative thereof, and a pharmaceutically acceptable salt thereof promote differentiation of myoblasts and restore muscle strength, thereby arriving at the present invention.

Solution to Problem

To address the aforementioned issues, one aspect of the present invention provides a compound represented by Formula 1 and a pharmaceutically acceptable salt thereof.

Another aspect of the present invention provides a pharmaceutical composition for preventing or treating a muscle weakness-related condition, comprising the compound or the pharmaceutically acceptable salt thereof, as an active ingredient.

Another aspect of the present invention provides a composition for promoting differentiation of myoblasts ex vivo, comprising the compound or the pharmaceutically acceptable salt thereof as an active ingredient.

Another aspect of the present invention provides a method of promoting myoblast differentiation, the method including treating myoblasts ex vivo with the compound or the pharmaceutically acceptable salt thereof.

Another aspect of the present invention provides a method of preparing myotubes, the method including treating myoblasts ex vivo with the compound or the pharmaceutically acceptable salt thereof to thereby differentiate the myoblasts.

Another aspect of the present invention provides a food composition for preventing or alleviating a muscle weakness-related condition, which comprises the compound represented by Formula 1 or a sitologically acceptable salt thereof.

Another aspect of the present invention provides a composition for muscle strength enhancement, comprising the compound or the pharmaceutically acceptable salt thereof as an active ingredient.

Another aspect of the present invention provides a method of preventing or treating a muscle weakness-related condition, the method including administering to a subject the compound represented by Formula 1 or the pharmaceutically acceptable salt thereof.

Another aspect of the present invention provides a use of the compound represented by Formula 1 or the pharmaceutically acceptable salt thereof, for preventing or treating a muscle weakness-related condition.

Another aspect of the present invention provides a use of the compound represented by Formula 1 or the pharmaceutically acceptable salt thereof, for the preparation of a medication for preventing or treating a muscle weakness-related condition.

Advantageous Effects of Invention

Alverine, 4-hydroxy alverine, a derivative thereof, or a pharmaceutically acceptable salt thereof of the present invention, when administered to myoblasts, promotes the same to differentiate into myotubes. Accordingly, alverine, 4-hydroxy alverine, a derivative thereof, or a pharmaceutically acceptable salt thereof of the present invention may be advantageously utilized in promoting the differentiation of myoblasts or preventing or treating a muscle weakness-related condition.

BRIEF DESCRIPTION OF DRAWINGS

FIG. 1 shows fluorescence images of myotubes that are differentiated by treating myoblasts with DMSO, insulin, or alverine citrate.

FIG. 2 shows graphs showing eMyHC fluorescent stained-areas in myotubes differentiated by treating myoblasts with DMSO, insulin, or alverine citrate.

FIG. 3 depicts a schedule of experiments using an animal to confirm a muscle strength enhancement effect of alverine citrate.

FIG. 4 is a graph showing measurement values of grip strength of mice according to the concentration of alverine citrate administered.

FIG. 5 shows the running time of mice in the normal group and experimental groups.

FIG. 6 is a graph showing the duration for which the mice in the normal group and experimental groups have clung onto a rotor-rod.

FIG. 7 is a graph showing muscle mass of gastrocnemius (GA) muscles and tibialis anterior (TA) obtained from the normal group mouse and the experimental group mice.

FIG. 8 depicts a schedule of experiments using a sarcopenia-induced animal to confirm a muscle strength enhancement effect of alverine citrate.

FIG. 9 shows the running time of mice in the normal group, the control group and experimental groups.

FIG. 10 shows a graph showing muscle mass of gastrocnemius (GA) muscles and tibialis anterior (TA) obtained from the mice in the normal group, the control group, and the experimental groups.

FIG. 11 shows fluorescent-staining images of myotubes that are differentiated by treating myoblasts with DMSO, insulin, alverine citrate, or 4-hydroxy alverine (4HA).

FIG. 12 shows graphs showing eMyHC fluorescent stained-areas in myotubes differentiated by treating myoblasts with DMSO, insulin, alverine citrate, or 4-hydroxy alverine (4HA).

FIG. 13 shows fluorescent-staining images of myotubes in which atrophy is induced by a cancer cell conditioned medium (CM) in alverine citrate (AC) or 4-hydroxy alverine (4HA).

FIG. 14 shows a graph of diameters of myotubes in which atrophy is induced by a cancer cell conditioned medium (CM) in alverine citrate (AC) or 4-hydroxy alverine (4HA).

FIG. 15 shows fluorescence-staining images of myotubes that are differentiated by treating myoblasts with DMSO, alverine, and 27 types of alverine derivatives, respectively.

FIG. 16 shows a graph showing an area of myotubes differentiated by treating myoblasts with DMSO, alverine, and 27 types of alverine derivatives, respectively.

BEST MODE FOR CARRYING OUT THE INVENTION

Hereinbelow, the present invention will be described in greater detail.

One aspect of the present invention provides a compound represented by Formula 1 below and a pharmaceutically acceptable salt thereof:

[Formula 1]

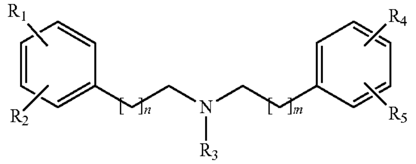

in Formula 1, $R_1$, $R_2$, $R_4$ and $R_5$ are each independently hydrogen, halogen, —$CF_3$, hydroxy, cyano, $C_{1-10}$ alkyl, $C_{1-10}$ alkoxy, $C_{1-4}$ haloalkyl, $C_{1-10}$ haloalkoxy, $C_{2-4}$ alkenyl, $C_{2-4}$ alkynyl, —$NHR_a$, —NHC(═O)$R_b$, —NHC(═O)$NHR_c$, amino-$C_{1-10}$ alkoxy, $C_{1-10}$ alkenyloxy, or $C_{6-10}$ aryl-$C_{1-10}$ alkoxy, $R_3$ is $C_{1-10}$ alkyl, $C_{2-12}$ alkenyl, $C_{1-4}$haloalkyl, $C_{2-4}$ alkenyl, or $C_{2-4}$ alkynyl, $R_a$ to $R_c$ are each independently, hydrogen, $C_{1-6}$ alkyl, $C_{1-6}$ alkoxy, $C_{1-4}$ haloalkyl, $C_{2-4}$ alkenyl, $C_{2-4}$ alkynyl, or $C_{6-10}$ aryl; and n and m are each independently an integer of 1 to 10.

The term "halo" or "halogen" as used herein, unless otherwise specified, refers to F, Cl, Br, or I.

The term "alkyl", unless otherwise indicated, refers to a straight chain or branched chain saturated hydrocarbon residue. For example, "$C_{1-10}$ alkyl" refers to an alkyl group having from 1 to 10 carbon atoms in its backbone structure. In particular, $C_{1-10}$ alkyl may include groups such as methyl, ethyl, n-propyl, i-propyl, n-butyl, i-butyl, t-butyl, n-pentyl, i-pentyl, t-pentyl, sec-pentyl, neopentyl, hexyl, heptyl, octyl, nonyl, and decyl.

The term "alkoxy" unless otherwise specified refers to a group having —O-alkyl structure in which an alkyl group as defined above is attached to a parent compound via an oxygen atom. The alkyl portion of an alkoxy group may contain from 1 to 20 carbon atoms (that is, $C_1$-$C_{20}$ alkoxy), from 1 to 12 carbon atoms (That is, $C_1$-$C_{12}$ alkoxy), or from 1 to 6 carbon atoms (that is, $C_1$-$C_6$ alkoxy). Examples of appropriate alkoxy groups include methoxy (—O—$CH_3$ or -OMe), ethoxy (—$OCH_2CH_3$ or -OEt), t-butoxy (—O—C$(CH_3)_3$ or —O-tBu), and the like.

The term "haloalkyl" refers to an alkyl group substituted by one or more halogen atoms. More specifically, a haloalkyl may be an alkyl group substituted by two or more of the same halogen, or substituted by two or more different halogens.

The term "haloalkoxy" refers to an alkoxy group substituted by one or more halogen atoms.

The term "aminoalkoxy" refers to an alkoxy group substituted by one or more amino groups.

The term "amino" refers to —$NR_2$ wherein "R" are each independently selected from among H, alkyl, aryl, and the like, and typical amino groups may include but are not limited to —$NH_2$, —$N(CH_3)_2$, —$NH(CH_3)$, —$N(CH_2CH_3)_2$, —$NH(CH_2CH_3)$, —NH (substituted or unsubstituted benzyl), —NH (substituted or unsubstituted phenyl), and the like.

The term "alkenyl" refers to a hydrocarbon having normal, secondary, tertiary, or cyclic carbon atoms having one or more unsaturated moieties, that is, carbon-carbon, $sp^2$ bonds. For example, the alkenyl group may contain from 2 to 20 carbon atoms (that is, $C_2$-$C_{20}$ alkenyl), from 2 to 12 carbon atoms (That is, $C_2$-$C_{12}$ alkenyl), or from 2 to 6 carbon atoms (that is, $C_2$-$C_6$ alkenyl). Examples of appropriate alkenyl groups include but are not limited to ethylene or vinyl(—CH═$CH_2$), allyl(—$CH_2$CH═$CH_2$), cyclopentenyl (—$C_5H_7$), and 5-hexenyl(—$CH_2CH_2CH_2CH_2$CH═$CH_2$).

The term "alkenyloxy" unless otherwise specified refers to a group having —O— alkenyl structure in which an alkenyl group as defined above is attached to a parent compound via an oxygen atom.

The term "alkynyl" refers to a hydrocarbon having normal, secondary, tertiary, or cyclic carbon atoms having one or more unsaturated moieties, that is, carbon-carbon, triple bonds. For example, the alkynyl group may contain from 2 to 20 carbon atoms (that is, $C_2$-$C_{20}$ alkynyl), from 2 to 12 carbon atoms (That is, $C_2$-$C_{12}$ alkynyl), or from 2 to 6 carbon atoms (that is, $C_2$-$C_6$ alkynyl). Appropriate alkynyl groups include, for example, acetylenic (—C≡H), propargyl (—$CH_2$C≡H) and the like, but are not limited thereto.

The term "aryl" as used herein refers to an aromatic hydrocarbon radical derived by the removal of one hydrogen atom from six carbon atoms of a parent aromatic ring system. For example, an aryl group may have from 6 to 20 carbon atoms, from 6 to 14 carbon atoms, or 6 to 12 carbon atoms.

The term "substitution" as used herein refers to substituting a hydrogen atom in a molecular structure with a substituent group, thereby becoming a chemically stable compound from such substitution, without exceeding the valence of a given atom. For example, the phrase "a group A is substituted with a substituent B" may mean that a hydrogen atom bound to an atom i.e., carbon, constituting the backbone of the group A is replaced with the substituent B, thereby forming a covalent bond between the group A and the substituent B.

According to one example, in Formula 1, $R_1$, $R_2$, $R_4$ and $R_5$ may be each independently hydrogen, halogen, hydroxy, $C_{1-10}$ alkyl, $C_{1-10}$ alkoxy, $C_{1-10}$ haloalkoxy, —$NHR_a$, —NHC(═O)$R_b$, —NHC(═O)$NHR_c$, amino $C_{1-10}$ alkoxy, $C_{1-10}$ alkenyloxy, or $C_{6-10}$ aryl-$C_{1-10}$ alkoxy, $R_3$ may be $C_{1-10}$ alkyl or $C_{2-12}$ alkenyl; $R_a$ to $R_c$ may be each independently hydrogen, $C_{1-6}$ alkyl, $C_{1-6}$ alkoxy, or $C_{6-10}$ aryl; and n and m may be each independently an integer of 1 to 7.

According to one example, in Formula 1, $R_1$ and $R_2$ may be each independently hydrogen, halogen, hydroxy, $C_{1-10}$ alkyl, $C_{1-10}$ alkoxy, $C_{1-10}$ haloalkoxy, —$NHR_a$, amino $C_{1-10}$ alkoxy, $C_{1-10}$ alkenyloxy, or $C_{6-10}$ aryl-$C_{1-10}$ alkoxy; $R_3$ may be $C_{1-10}$ alkyl, $R_4$ and $R_5$ may be each independently hydrogen, hydroxy, —$NHR_a$, —NHC(═O)$R_b$, or —NHC(═O)$NHR_c$; $R_a$ to $R_c$ may be each independently hydrogen, $C_{1-4}$ alkyl, $C_{1-6}$ alkoxy, or $C_{6-10}$ aryl; and n and m may be each independently an integer of 1 to 5.

According to another example, in Formula 1, $R_1$ and $R_2$ may be each independently hydrogen, halogen, hydroxy, $C_{1-6}$ alkyl, $C_{1-6}$ alkoxy, $C_{1-6}$ haloalkoxy, —$NHR_a$, amino $C_{1-10}$ alkoxy, $C_{1-10}$ alkenyloxy, or $C_{6-10}$ aryl-$C_{1-6}$ alkoxy, $R_3$ may be $C_{1-6}$ alkyl, $R_4$ may be hydrogen, halogen, hydroxy, —$NHR_a$, —NHC(═O)$R_b$, or —NHC(═O)$NHR_c$, and $R_5$ may be hydrogen; $R_a$ may be hydrogen or $C_{1-6}$ alkoxy; $R_b$ may be hydrogen or $C_{1-6}$ alkyl; $R_c$ may be hydrogen or $C_{6-10}$ aryl; and n and m may be each independently an integer of 1 to 3.

According to another example, in Formula 1, if n and m are each 2, $R_3$ is ethyl, and $R_1$, $R_4$, and $R_5$ are each hydrogen, and $R_2$ is hydrogen or hydroxy. In this case, this example may be an alverine or 4-hydroxy alverine.

In particular, the alverine has the structure represented in Formula 2 below.

[Formula 2]

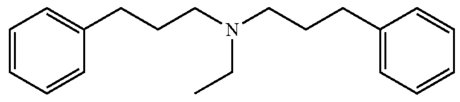 [SMILES: CCN(CCCc1ccccc1)CCCc1ccccc1]

Here, the alverine corresponds to the compound of Formula 1 when n and m are each 2, $R_3$ is ethyl, and $R_1$, $R_2$, $R_4$, and $R_5$ are all hydrogen.

The term "alverine" as used herein refers to a compound that has the IUPAC name of N-ethyl-3-phenyl-N-(3-phenylpropyl)propan-1-amine, chemical formula of $C_{20}H_{27}N$ and a molecular weight of 281.44 g/mol. The alverine is generally known as a drug used for gastrointestinal disorders, but little is known about its relation to myoblast differentiation.

In addition, the 4-hydroxy alverine is a metabolite of alverine, and the 4-hydroxy alverine has the structure of Formula 3 below.

[Formula 3]

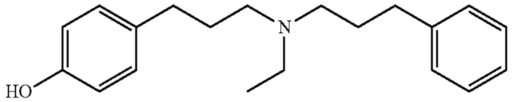

Here, the 4-hydroxy alverine corresponds to a compound of Formula 1 when n and m are each 2, $R_3$ is ethyl, and among $R_1$, $R_2$, $R_4$, and $R_5$, three are hydrogen and one is hydroxy. In particular, the case in which among $R_1$, $R_2$, $R_4$ and $R_5$, three are hydrogen and one is hydroxy may include the following cases: 1) $R_2$, $R_4$, and $R_5$ are each hydrogen, and $R_1$ is hydroxy; 2) $R_1$, $R_4$ and $R_5$ are each hydrogen and $R_2$ is hydroxy; iii) $R_1$, $R_2$, and $R_5$ are each hydrogen and $R_4$ is hydroxy; and iv) $R_1$, $R_2$, and $R_4$ are each hydrogen and $R_5$ is hydroxy.

According to a specific example, specific examples of the compound represented by Formula 1 include the following:

1) 4-(3-ethyl(3-phenylpropyl)amino)propyl)aniline;
2) N-ethyl-3-(4-methoxyphenyl)-N-(3-phenylpropyl)propan-1-amine;
3) N-ethyl-3-phenyl-N-(3-(p-tolyl)propyl)propan-1-amine;
4) 3-(3-(ethyl(3-phenylpropyl)amino)propyl)phenol;
5) N-methyl-3-phenyl-N-(3-phenylpropyl)propan-1-amine;
6) 4,4'-((ethylazanediyl))bis(propan-3,1-diyl))diphenol;
7) 4-(3-(methyl(3-phenylpropyl)amino)propyl)phenol;
8) 4-(3-((3-(4-(benzyloxy)phenyl)propyl)(ethyl)amino)propyl)aniline;
9) N-(4-(3-((3-)4-(benzyloxy)phenyl)propyl)(ethyl)amino)propyl)phenyl)acetamide;
10) 4-(3-(ethyl(phenethyl)amino)propyl)phenol;
11) 4-(3-(ethyl(3-phenylpropyl)amino)propyl)-2-fluorophenol;
12) 2-bromo-4-(3-(ethyl(3-phenylpropyl)amino)propyl)phenol;
13) 1-(4-(3-((3-(4-(benzyloxy)phenyl)propyl)(ethyl)amino)propyl)phenyl)-3-phenylurea;
14) ethyl(4-phenylbutyl)(3-phenylpropyl)amine;
15) ethyl bis(4-phenylbutyl)amine;
16) (4-phenylbutyl)(3-phenylpropyl)propylamine;
17) 3-(4-butoxyphenyl)-N-ethyl-N-(3-phenylpropyl)propan-1-amine;
18) 3-(4-(but-3-en-1-yloxy)phenyl)-N-ethyl-N-(3-phenylpropyl)propan-1-amine;
19) 3-(4-(4-bromobutoxy)phenyl)-N-ethyl-N-(3-phenylpropyl)propan-1-amine;
20) 4-(4-(3-(ethyl(3-phenylpropyl)amino)propyl)phenoxy)butan-1-amine;
21) 4-(3-(ethyl(3-(4-methoxyphenyl)propyl)amino)propyl)-2-fluorophenol;
22) 4-(3-((3-(4-(benzyloxy)-3-fluorophenyl)propyl)(ethyl)amino)propyl)aniline;
23) N-(4-(3-((3-(4-(benzyloxy)-3-fluorophenyl)propyl)(ethyl)amino)propyl)phenyl)acetamide;
24) 3-(4-(benzyloxy)-3-fluorophenyl)-N-methyl-N-(3-phenylpropyl)propan-1-amine;
25) 4-(3-(ethyl(3-(p-tolyl)propyl)amino)propyl)-2-fluorophenol;
26) N-ethyl-3-phenyl-N-(3-(4-(3-phenylpropoxy)phenyl)propyl)propan-1-amine;
27) N-ethyl-3-phenyl-N-(3-(4-((5-phenylpentyl)oxy)phenyl)propyl)propan-1-amine;
28) N-ethyl-3-phenyl-N-(3-phenylpropyl)propan-1-amine (that is, alverine); and
29) 4-[3-[ethyl(3-phenylpropyl)amino]propyl]phenol (that is, 4-hydroxy alverine).

As used herein, the term "pharmaceutically acceptable salt" refers to a salt prepared according to a common method known in the art, and such preparation methods are known to those skilled in the art. In particular, the pharmaceutically acceptable salt includes pharmacologically, or physiologically acceptable salts derived from the following inorganic acids, organic acids, and bases, but are not limited thereto. Examples of suitable such acids may include hydrochloric acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, and the like. Salts derived from suitable bases may include alkali metals such as sodium or potassium, and alkaline earth metals such as magnesium. In particular, the pharmaceutically acceptable salt may be a citrate. In one example of the present invention, a citrate was used as the pharmaceutically acceptable salt.

Another aspect of the present invention provides a pharmaceutical composition for preventing or treating a muscle weakness-related condition, comprising the compound represented by Formula 1 or a pharmaceutically acceptable salt thereof, as an active ingredient. Here, the compound represented by Formula 1 or a pharmaceutically acceptable salt thereof are the same as described above.

The muscle weakness-related condition refers to any and all conditions caused by muscle weakness, and particularly, conditions which have reduced or weakened potency of myoblasts due to reduced muscle cells in the body or reduced activity of satellite cells, and therefore are expected to be preventable, alleviable, or treatable by promoting myoblast differentiation. In particular, the muscle weakness-related condition may be sarcopenia, muscular atrophy, muscular dystrophy, or cachexia.

The term "sarcopenia" as used herein refers to a symptom characterized by a gradual decrease in muscle mass caused by aging which results in a decrease in muscle strength. As the cause of the decrease in muscle mass in sarcopenia, the decrease in the activity of satellite cells is considered as a major cause. Satellite cells are activated by stimuli, such as exercise or injury, to proliferate into myoblasts, and as differentiation proceeds, fuse with other cells to form multinucleated muscle fibers.

As used herein, the term "muscular atrophy" refers to a symptom characterized by gradual atrophy of the muscles in the extremities in a near-symmetrical manner. Muscular atrophy may cause progressive degeneration of motor nerve fibers and cells in the spinal cord, and may cause amyotrophic lateral sclerosis (ALS) and spinal progressive muscular atrophy (SPMA) The term "muscular dystrophy" as used herein refers to a degenerative muscular disease characterized by necrosis in muscle fibers regardless of the central nervous system and the peripheral nervous system. There is a slight clinical difference between muscular dystrophy and muscular atrophy. The most common onset for muscular dystrophy beings in childhood, and the onset for muscular atrophy usually occurs in the teenage years. In addition, muscular dystrophy occurs in the proximal muscles and muscular atrophy occurs in the distal muscles. Muscle stiffness is present in muscular dystrophy but absent in muscular atrophy, and while muscular dystrophy is a clearly hereditary condition, but muscular atrophy is rarely inherited.

The term "cachexia" as used herein refers to a severe systemic weakening that can be seen in the terminal stages of cancer, tuberculosis, hemophilia, and the like. In addition, cachexia is regarded as an intoxication state caused by various organ dysfunctions inside the body. Symptoms of cachexia include muscle weakness, rapid weight loss, anemia, lethargy, and yellowing of the skin. Some of the underlying conditions that may cause cachexia include malignant tumors, Basedo's disease, and hypopituitarism. Bioactive substances such as tumor necrosis factor (TNF) produced by macrophages were also found to be factors that aggravate cachexia.

In the pharmaceutical composition, the concentration of the compound represented by Formula 1 or a pharmaceutically acceptable salt thereof may be from 10 g/ml to 180 μg/ml. More particularly, the concentration of the compound represented by Formula 1 or a pharmaceutically acceptable salt thereof may be from 20 g/ml to 160 g/ml, from g/ml to 140 g/ml, or from 60 g/ml to 120 g/ml.

In addition, the dose of the pharmaceutical composition may be determined based on the amount of the active ingredient being administered, which is the compound represented by Formula 1 or a pharmaceutically acceptable salt thereof. In particular, the dose of the compound represented by Formula 1 or a pharmaceutically acceptable salt thereof may be from 60 mg to 240 mg daily, and for high doses, the administration may be made over 1 to 3 separate administrations over the course of a day. Preferably, the dose of the compound represented by Formula 1 or a pharmaceutically acceptable salt thereof is from 60 mg to 120 mg, which may be administered once or twice a day.

The pharmaceutical composition may optionally include a pharmaceutically acceptable carrier. The carrier is one commonly used in the manufacture of drugs, and may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, and the like.

The pharmaceutical composition may further include a pharmaceutically acceptable additive selected from the group consisting of lubricants, wetting agents, sweetening agents, flavoring agents, emulsifying agents, suspending agents, preservatives, and a combination thereof.

The pharmaceutical composition may be appropriately administered to a subject according to a method, administration route, and dose commonly used in the art. In particular, appropriate dose and appropriate dosing frequency of the pharmaceutical composition may be selected according to a method known in the art, and the dose and dosing frequency of the pharmaceutical composition in practice may be determined by various factors such as the type of symptom to be prevented or treated, an administration route, sex, physical state, diet, a subject's age and body weight and severity of the disease, and the like.

Another aspect of the present invention provides a composition for promoting differentiation of myoblasts ex vivo, comprising the compound represented by Formula 1 or a pharmaceutically acceptable salt thereof as an active ingredient. Here, the compound represented by Formula 1 or a pharmaceutically acceptable salt thereof are as described above.

The term "ex vivo" as used herein refers to the state of a part of a living organism, such as cells or tissues, being extracted and isolated 'outside a living organism'. In particular, ex vivo may mean "in vitro" to perform an experiment on a part of a living organism under artificial conditions.

The myoblasts refer to muscle cells in an undifferentiated state. In differentiation of the myoblasts, mononuclear myoblasts fuse into multinucleated myotubes. During terminal differentiation of myoblasts, the expression of myosin heavy chain (MyHC) is increased.

The composition for promoting differentiation may be a DMEM differentiation medium containing serum but may include any medium or composition capable of promoting differentiation of myoblasts without limitations. In addition, the composition may further include additional materials required for cell growth or differentiation.

In the pharmaceutical composition, the concentration of the compound represented by Formula 1 or a pharmaceutically acceptable salt thereof may be from 0.01 μM to 100 μM. In particular, the concentration of the compound represented by Formula 1 or a pharmaceutically acceptable salt thereof may be from 0.1 μM to 50 μM, from 0.1 μM to M, from 0.5 μM to 25 μM, from 0.1 μM to 10 μM, from 0.5 μM to 10 μM, from 1 M to 10 μM, from 0.1 μM to 5 μM, from 0.5 μM to 5 μM, from 1 μM to 5 μM, from 0.1 M to 2 μM, from 0.5 μM to 2 μM, or from 1 μM to 2 μM. In one example of the present invention, the compound represented by Formula 1 or a pharmaceutically acceptable salt thereof was administered to mouse-derived myoblasts C2Cl2 cells at a concentration of 1 μM.

Another aspect of the present invention provides a method of promoting myoblast differentiation, which includes treating myoblasts ex vivo with the compound represented by Formula 1 or a pharmaceutically acceptable salt thereof. The method of promoting myoblast differentiation may be performed in vitro or ex vivo.

Another aspect of the present invention provides a method of preparing myotubes, which includes treating myoblasts ex vivo with the compound represented by Formula 1 or a pharmaceutically acceptable salt thereof to thereby differentiate the myoblasts. The method of preparing myotubes may be performed in vitro or ex vivo.

Another aspect of the present invention provides a food composition for preventing or alleviating a muscle weakness-related condition, which includes the compound represented by Formula 1 or a sitologically acceptable salt thereof. The food composition, when used as a food additive, may be added as is, or used in combination with other food ingredients, and may be appropriately used according to common methods.

In order to prevent or alleviate a muscle weakness-related condition, the food composition may be used at the same time, or independently from, a medication used for disease treatment, before or after the development of the muscle weakness-related condition. In particular, the food composition is characterized by promoting the differentiation of myoblasts. The muscle weakness-related condition is the same as described with respect to the pharmaceutical composition above.

Another aspect of the present invention provides a composition for muscle strength enhancement, which includes the compound represented by Formula 1, a pharmaceutically acceptable salt thereof, or a sitologically acceptable salt thereof, as an active ingredient. The composition for muscle strength enhancement may be used as a pharmaceutical composition or a food composition.

The muscle strength enhancement refers to increase in muscle weight, enhancement of muscle recovery, and decrease in muscle fatigue. The composition for muscle strength enhancement may through the ability to differentiate myoblasts to muscle cells, can increase muscle mass and subsequently the overall muscle mass, and as a result, muscle fatigue can decrease. In addition, rapid replacement of muscle cells permits quick recovery from muscle injuries. The composition for muscle strength enhancement of the present invention may be used as feed or a feed additive.

Another aspect of the present invention provides a method of preventing or treating a muscle weakness-related condition, the method including administering to a subject the compound represented by Formula 1 or a pharmaceutically acceptable salt thereof. Here, the compound, muscle weakness-related condition and subject are the same as described above.

Another aspect of the present invention provides a use of the compound represented by Formula 1 or a pharmaceutically acceptable salt thereof, for preventing or treating a muscle weakness-related condition. Here, the compound and muscle weakness-related condition are the same as described above.

Another aspect of the present invention provides a use of the compound represented by Formula 1 or a pharmaceutically acceptable salt thereof, for preparing a medication for preventing or treating a muscle weakness-related condition. Here, the compound and muscle weakness-related condition are the same as described above.

MODE FOR THE INVENTION

Hereinafter, the present invention is explained in detail by Examples. The following Examples are intended to further illustrate the present invention without limiting its scope.

Experimental Example 1. Confirmation of the Effect of Alverine Citrate on Promoting Myoblast Differentiation

Experimental Example 1.1. Culture of Myoblast Cell Line C2C12

C2C12 (American Type Culture Collection, CRL-1772™) cells are a myoblast cell line obtained from C3H mouse and is used in myoblast differentiation research. The C2C12 cells were cultured using growth media, and then cultured using differentiation media for differentiation induction. Here, DMEM supplemented with 10% fetal bovine serum was used as growth media (GM), and DMEM supplemented with 5% horse serum (HS) was used as differentiation media (DM).

Experimental Example 1.2. Promotion of Differentiation of Myoblasts

In order to confirm the effect of alverine citrate on promoting the differentiation of myoblasts, C2C12 cells were dispensed in the GM of Example 1.1 and cultured for 24 hours, and then the C2C12 cells were treated with DMSO, insulin, or alverine citrate, and induced for differentiation over 3 days. Subsequently, by florescent staining using antibodies against myosin H chain (hereinbelow, MyHC), the cells were observed for differentiation to myotubes and changes in myotube thickness and diameters. Here, the DMSO, insulin and alverine citrate used in the experiment were all purchased from Sigma-Aldrich. The group treated with insulin was used as the positive control group.

In particular, C2C12 cells were dispensed in a 6-well plate treated with the GM of Example 1.1 at a concentration of $5\times10^5$ cells per plate and after 24 hours, were replaced with DMEM media supplemented with 5% HS and induced for differentiation. Thereafter, the cells were treated with DMSO, insulin (1.72 μM) or alverine citrate (0.01 μM, 0.1 μM, 1 μM or 10 μM). After 3 days, after removing the media, the cells were washed with phosphate buffer solution (lx PBS) and treated with paraformaldehyde (4%) and fixed at room temperature for 15 minutes. Then, after washing three times with phosphate buffer solution (1×PBS), PBS containing 0.3% triton X-100 was treated with permeabilization buffer and allowed to react at room temperature for 10 minutes.

After washing three times with phosphate buffer solution (1×PBS), PBST (blocking buffer, PBS containing 0.5% Tween 20) containing 2% bovine serum albumin was administered and allowed to react for 30 minutes to suppress nonspecific binding of antibodies. After washing with phosphate buffer (1×PBS) three times, 100 μL of primary antibodies (SC-20641, Santa Cruz Biotechnology) to MYH3 diluted to 1:500 were added and allowed to react at room temperature for 1 hour. Thereafter, after washing with phosphate buffer (1×PBS) three times, 100 μL of secondary antibodies (Goat anti-Rabbit IgG-HRP) diluted to 1:5,000 were added and allowed to react at room temperature for 1 hour. After 1 hour, for nuclear staining, after washing with phosphate buffer (1×PBS) three times, the blocking buffer was treated with diluted DAPI dye and allowed to react at room temperature for 10 minutes. Thereafter, after washing with phosphate buffer (1×PBS) three times, the washed cover glass was measured for absorbance at a wavelength of 450 nm and a fluorescent image was taken using a fluorescence microscope. The anti-MyHC antibody stained area was analyzed using imageJ (Java-based image processing program).

As a result, it was found that the myoblasts treated with insulin or alverine citrate were more differentiated to myotubes than the myoblasts treated with DMSO alone. Particularly, as the treatment concentration of alverine citrate increases, the diameter of myotubes increased (FIG. 1 and FIG. 2).

Experimental Example 2. Confirmation of Muscle Strength Enhancement Effect of Alverine Citrate, Using Normal Mouse In order to confirm the muscle strength enhancement effect of alverine citrate, after administering alverine citrate to a mouse, the mouse was tested for motor functions such as grip strength, running, balance coordination, and the like. After motor function tests, muscle weight was measured. In particular, each of 10 week-old C57BL/6 male mice was dosed orally with 200 μL of alverine citrate for 4 weeks, at a daily dose of 17 mg/kg/day (AC-L), 50 mg/kg/day (AC-M) or 150 mg/kg/day (AC-H). This group of mice was set as the experimental group (FIG. 3). The 10 week-old C57BL/6 male mice were purchased from Daehan BioLink.

Experimental Example 2.1. Grip Strength Measurement

Grip strength was measured using a grip strength meter for mice (Bioseb, USA). In particular, the mice were placed on a metal grid connected to an instrument panel through which grip strength can be monitored, and while pulling the mice back by tail, the grip strength by which the mice grabbed the metal grid was measured. Here, 5 consecutive, repeated measurements were recorded and an average value of the 5 measurements was calculated.

As a result, the grip strength of the mice in the experimental group was higher than that of the mouse in the normal group. Through the above, it was confirmed that the alverine citrate has a muscle strength enhancement effect (FIG. 4).

Experimental Example 2.2. Running Ability Test

Running ability was measured using a treadmill designed specific for this experiment. First, aversive stimuli were provided by letting electric stimuli flow at the starting point. Before the measurement, the mice were acclimatized at 8 m/min for 10 minutes. The running time was recorded by allowing mice in each group to run in separate lanes until exhaustion. Exhaustion was defined such that when the mouse stays outside the lanes for 10 seconds or more without running, the mouse was determined to be exhausted and the time was recorded. It was not possible to repeat this experiment on the same mouse. The mouse was placed on the treadmill and the test was started at 8 rpm, and the speed was accelerated by 2 rpm every 10 minutes to a maximum speed of 20 rpm. The slope of the lane started from a zero-degree incline and then was elevated to a five-degree incline after 30 min from the start.

The result shows that the running time of the experimental group mice increased compared to the normal group mouse, and in particular, a significant increase in the running time was observed in the experimental group treated with 150 mg/kg/day alverine citrate (FIG. 5).

Experimental Example 2.3. Balance Coordination Test

Balance coordination was measured using a rota-rod test. The rota-rod test device consists of 4 test zones, each having a shaft diameter of 3 cm and a lane width of 9 cm, and 5 rotatable circular dividers having a diameter of 60 cm and a round rod. The test was started from a rotating speed of 10 rpm, and the speed was accelerated up to maximum 40 rpm over 5 minutes, and the duration for which the mouse remains inside the rota-rod device, clinging to the round rod without falling, was recorded. The mouse was allowed to rest for 15 minutes after each test and was subjected to three tests in total. An average value of three measurements was calculated.

The result shows that the duration for which the experimental group mice clung onto the round rod increased compared to the normal group mouse, and as the administration dose of alverine citrate increased, the duration for which the experimental group mice clung to the round rod also increased proportionally (FIG. 6).

Experimental Example 2.4. Muscle Weight Measurement

For muscle weight measurement, gastrocnemius (GA) tibialis anterior (TA) muscles in the hindlimb of the mice in each group were removed and weighed. The result shows that the muscle weight of GA and TA in the experimental group mice increased compared to the normal group mouse, and in particular, as the administration dose of alverine citrate increases, the muscle weight of GA and TA in the experimental group mice also increased (FIG. 7).

Experimental Example 3. Confirmation of Muscle Strength Enhancement Effect of Alverine Citrate Using Sarcopenia-Induced Mouse In order to confirm a muscle strength enhancement effect of alverine citrate, sarcopenia-induced mice were administered with alverine citrate and tested for running ability. After the treadmill running test, muscle weight was measured. In particular, the hindlimb of 10 week-old C57BL/6 male mice was immobilized using a surgical stapler (Autosuture Royal 35W stapler). The staples were removed after 5 days and the mice were allowed to remobilize for 3 days. After that, running ability was measured. The mice were dosed orally with 200 μL of alverine citrate per mice at a dose of 17 mg/kg/day (AC-L), 50 mg/kg/day (AC-M) or 150 mg/kg/day (AC-H), and these mice were set as the experimental group. Untreated sarcopenia-induced mice were set as the control group (FIG. 8). The 10 week-old C57BL/6 male mice were purchased from Daehan BioLink.

Experimental Example 3.1. Running Ability Test

Running ability was measured by the same method as in Example 2.2. As a result, it was found that the running time of the control group mice was decreased by about 10 minutes compared to the normal group mouse. On the other hand, the running time of the experimental group mice increased proportionally with the dose concentration of alverine citrate, and in particular, the running time of the experimental group orally given a dose of 150 mg/kg/day (AC-H) of alverine increased compared to the normal mouse.

Experimental Example 3.2. Muscle Weight Measurement

For muscle weight measurement, the GA and TA muscles in the hindlimb of the mice in each group were removed and weighed. As a result, it was found that there was a significant decrease in the GA and TA muscle weight of the control group, compared to the normal group. However, in case of the experimental group, as the dose concentration of alverine citrate increased, the GA and TA muscle weights of the experimental group mice also increased (FIG. 10).

Experimental Example 4. Confirmation of the Effect of 4-Hydroxy Alverine on Promoting Myoblast Differentiation To confirm the effect of 4-hydroxy alverine on promoting myoblast differentiation, following the same method as Example 1, DMSO, insulin (1.72 μM), alverine citrate (0.01 μM, 0.1 μM, 1 μM or 10 μM), 4-hydroxy alverine (0.01 μM, 0.1 μM, 1 μM or 10 M) were each administered, and differentiation to myotubes and changes in myotube thickness and diameter were observed. Here, the alverine and 4-hydroxy alverine are shown in Table 1.

[Table 1]

| Name | Structural Formula | IUPAC Name | Formula |
|---|---|---|---|
| Alverine | 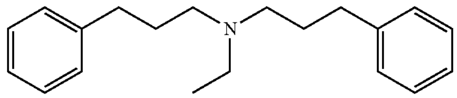 | N-ethyl-3-phenyl-N-(3-phenylpropyl) propan-1-amine | C20H27N |
| 4-Hydroxy alverine | 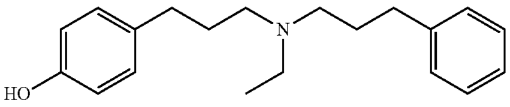 [SMILES: CCN(CCCc1ccccc1)CCCc1ccc(O)cc1] | 4-[3-Ethyl(3-phenylpropyl) amino] propyl)phenol | C20H27NO |

As a result, it was found that the myoblasts treated with alverine citrate or 4-hydroxy alverine were more differentiated to myotubes than the myoblasts treated with DMSO or insulin (FIG. 11 and FIG. 12). When compared at the same concentration, 4-hydroxy alverine had superior differentiation promoting effect than alverine.

Experimental Example 5. Confirmation of Cachexia Treatment Effect of Alverine Citrate and 4-Hydroxy Alverine In order to confirm a cachexia treatment effect of alverine citrate and 4-hydroxy alverine, an experiment mimicking a tumor-growth environment by treatment of a cancer cell conditioned medium (CM) was conducted as an ex vivo approach. First, cancer cell CM was prepared using a C26 cancer cell line. Here, as cancel cell growth media (GM), RPMI1640 media supplemented with 10% fetal bovine serum was used. The C26 cancer cell line was cultured using a 100 mm cell culture plate and the cancer cell GM. Here, the media were removed when cell confluency reached 90%. Then, after washing with phosphate buffer (1× buffer), the prepared differentiation media were treated following the same process as in Example 1. After 24 hours, a C26 cancer cell line CM was obtained and filtered using bottle top filters (Thermo, PES, 1L) before use.

C2C12 cells were dispensed in a 6-well plate treated with the GM of Example 1.1 at a concentration of $5\times10^5$ cells per plate and after 24 hours, were replaced with DMEM media supplemented with 5% HS and induced for differentiation. After 4 days, differentiated myotubes were treated with differentiation media supplemented with 33% CM and induced for myotube atrophy for 3 days. Here, by treating the experimental groups with 1 μM alverine citrate (AC) and 4-hydroxy alverine (4HA), the effect of suppressing myotube atrophy was evaluated. DMSO was used as the negative control group, and ursolic acid (UA) was used as the positive control group. Following the same method as in Example 1.2, by florescent staining using antibodies against MyHC, the expression amount of MyHC was measured.

As a result, it was found that myotubes in the negative control group were atrophied by CM. On the other hand, it was found that myotube atrophy was suppressed when treated with alverine citrate or 4-hydroxy alverine (FIG. 13 and FIG. 14).

Example 1. Confirmation of the Effect of Alverine Derivatives on Promoting Myoblast Differentiation

Example 1.1. Growth of Myoblast Cell Line C2C12

C2Cl2 (American Type Culture Collection, CRL-1772™) cells are a myoblast cell line obtained from C3H mouse and is used in myoblast differentiation research. The C2Cl2 cells were cultured using growth media, and then cultured using differentiation media for differentiation induction. Here, DMEM supplemented with 10% fetal bovine serum was used as growth media (GM), and DMEM supplemented with 5% horse serum (HS) was used as differentiation media (DM).

Example 1.2. Acceleration of Differentiation of Myoblast Cell Line

In order to confirm the effect of an alverine derivative on promoting the differentiation of myoblasts, C2C12 cells were dispensed in the GM of Example 1.1 and cultured for 24 hours. Then, the C2C12 cells were treated with DMSO (Sigma-Aldrich), insulin, alverine (Sigma-Aldrich), or 27 types of alverine derivatives, each at a concentration of 1 μM and were induced for differentiation over 4 days. Subsequently, florescent staining using antibodies against MyHC was used to monitor differentiation to myotubes and changes in myotube thickness and diameter. Here, the 27 types of alverine derivatives were designed and synthesized by Korea Research Institute of Bioscience and Biotechnology and JD Bioscience, upon request, and the alverine and the 27 types of alverine derivatives 1 to 27 used in the experiment are shown in Table 2 below.

TABLE 2

| Derivative name | Structural formula | IUPAC Name |
|---|---|---|
| Alverine | 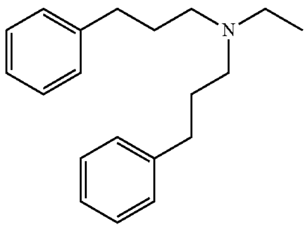 [SMILES: CCN(CCCc1ccccc1)CCCc1ccccc1] | N-ethyl-3-phenyl-N-(3-phenylpropyl) propan-1-amine |

TABLE 2-continued
| Derivative name | Structural formula | IUPAC Name |
| --- | --- | --- |
| 1 | 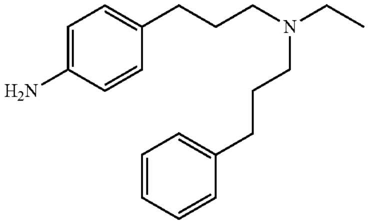 [SMILES: CCN(CCCc1ccccc1)CCCc1ccc(N)cc1] | 4-(3-(ethyl(3-phenylpropyl)amino)propyl) aniline |
| 2 | 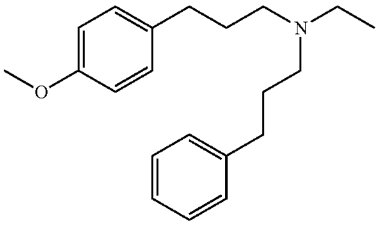 [SMILES: CCN(CCCc1ccccc1)CCCc1ccc(OC)cc1] | N-ethyl-3-(4-methoxyphenyl)-N-(3-phenylpropyl)propan-1-amine |
| 3 | 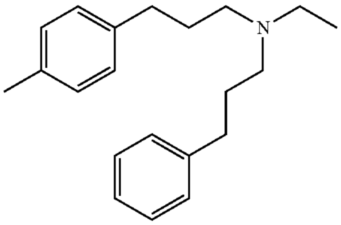 [SMILES: CCN(CCCc1ccccc1)CCCc1ccc(C)cc1] | N-ethyl-3-phenyl-N-(3-(p-tolyl)propyl)propan-1-amine |
| 4 | 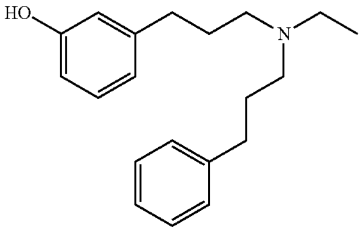 [SMILES: CCN(CCCc1ccccc1)CCCc1cccc(O)c1] | 3-(3-(ethyl(3-phenylpropyl)amino)propyl)phenol |
| 5 | 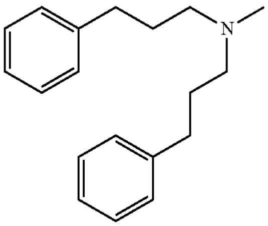 [SMILES: CN(CCCc1ccccc1)CCCc1ccccc1] | N-methyl-3-phenyl-N-(3-phenylpropyl)propan-1-amine |
| 6 | 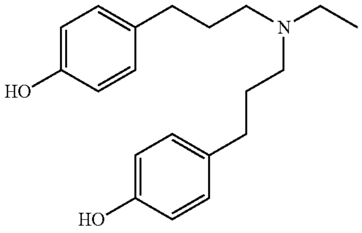 [SMILES: CCN(CCCc1ccc(O)cc1)CCCc1ccc(O)cc1] | 4,4'-((ethylazanediyl)bis (propane-3,1-diyl))diphenol |

TABLE 2-continued
| Derivative name | Structural formula | IUPAC Name |
| --- | --- | --- |
| 7 | 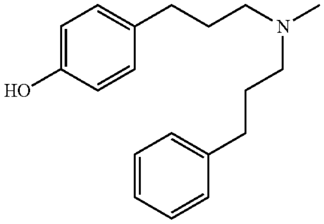 [SMILES: CN(CCCc1ccccc1)CCCc1ccc(O)cc1] | 4-(3-(methyl(3-phenylpropyl) amino)propyl)phenol |
| 8 | 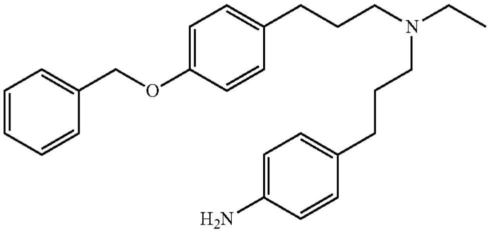 [SMILES: CCN(CCCc1ccc(N)cc1)CCCc1ccc(OCc2ccccc2)cc1] | 4-(3-((3-(4-(benzyloxy)phenyl) propyl)(ethyl)amino)propyl)aniline |
| 9 | 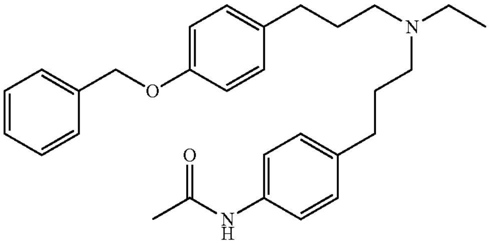 [SMILES: CCN(CCCc1ccc(NC(C)=O)cc1)CCCc1ccc(OCc2ccccc2)cc1] | N-(4-(3-((3-(4- (benzyloxy)phenyl)propyl(ethyl) amino)propyl)phenyl)acetamide |
| 10 | 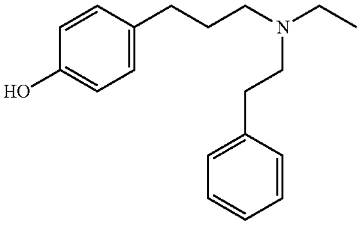 [SMILES: CCN(CCCc1ccc(O)cc1)CCc1ccccc1] | 4-(3-(ethyl(phenethyl)amino) propy)phenol |
| 11 | 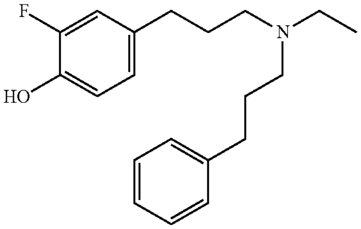 [SMILES: CCN(CCCc1ccccc1)CCCc1ccc(O)c(F)c1] | 4-(3-(ethyl(3-phenylpropyl)amino) propyl)-2-fluorophenol |
| 12 | 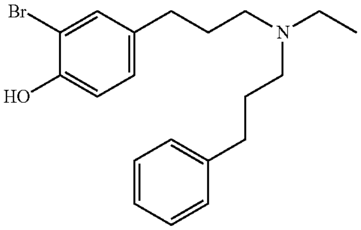 [SMILES: CCN(CCCc1ccccc1)CCCc1ccc(O)c(Br)c1] | 2-bromo-4-(3-(ethyl(3- phenylpropyl)amino)propyl)phenol |

TABLE 2-continued
| Derivative name | Structural formula | IUPAC Name |
|---|---|---|
| 13 | 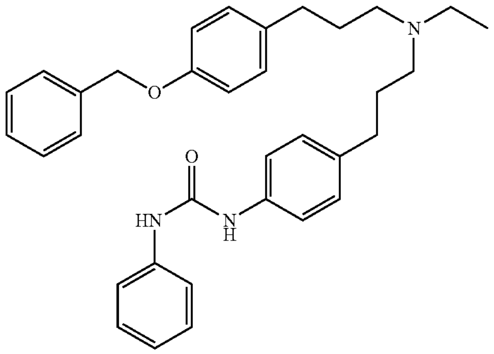 [SMILES: CCN(CCCc1ccc(NC(=O)Nc2ccccc2)cc1)CCCc1ccc(OCc2ccccc2)cc1] | 1-(4-(3-((3-(4-(benzyloxy)phenyl)propyl)(ethyl)amino)propyl)phenyl)-3-phenylurea |
| 14 | 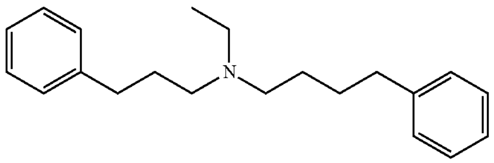 [SMILES: CCN(CCCCc1ccccc1)CCCc1ccccc1] | Ethyl(4-phenylbutyl)(3-phenylpropyl)amine |
| 15 | 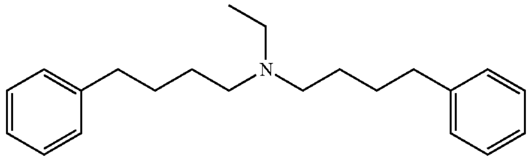 [SMILES: CCN(CCCCc1ccccc1)CCCCc1ccccc1] | Ethylbis(4-phenylbutyl)amine |
| 16 | 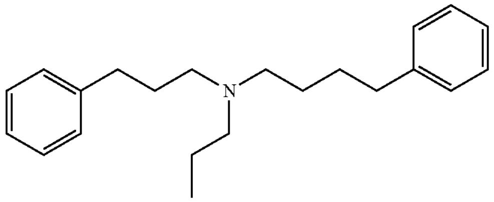 [SMILES: CCCN(CCCCc1ccccc1)CCCc1ccccc1] | (4-phenylbutyl)(3-phenylpropyl)propylamine |
| 17 | 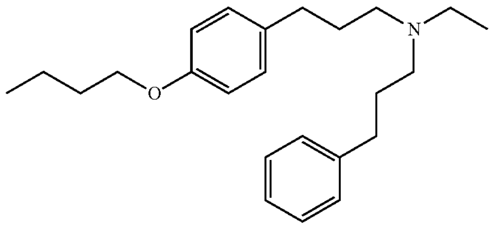 [SMILES: CCCCOc1ccc(CCCN(CC)CCCc2ccccc2)cc1] | 3-(4-butoxyphenyl)-N-ethyl-N-(3-phenylpropyl)propan-1-amine |
| 18 | 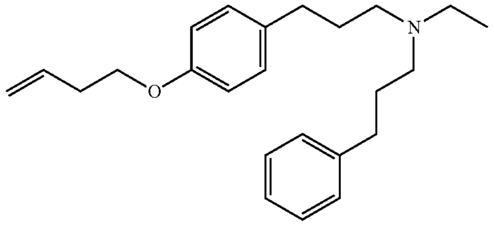 [SMILES: C=CCCOc1ccc(CCCN(CC)CCCc2ccccc2)cc1] | 3-(4-(but-3-en-1-yloxy)phenyl)-N-ethyl-N-(3-phenylpropyl)propan-1-amine |

TABLE 2-continued

| Derivative name | Structural formula | IUPAC Name |
|---|---|---|
| 19 | 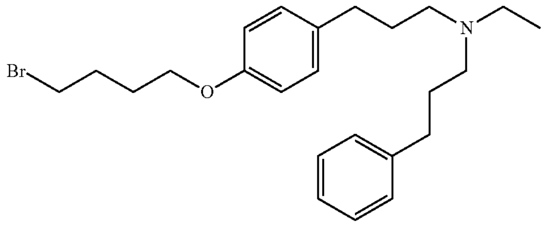 [SMILES: CCN(CCCc1ccccc1)CCCc1ccc(OCCCCBr)cc1] | 3-(4-(4-bromobutoxy)pbenyl)-N-ethyl-N-(3-phenylpropyl)propan-1-amine |
| 20 | 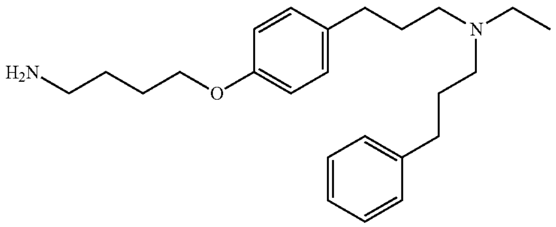 [SMILES: CCN(CCCc1ccccc1)CCCc1ccc(OCCCCN)cc1] | 4-(4-(3-(ethyl(3-phenylpropyl)amino)propyl) phenoxy)butan-1-amine |
| 21 | 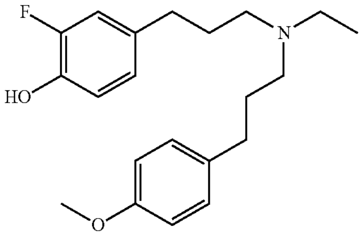 [SMILES: CCN(CCCc1ccc(OC)cc1)CCCc1ccc(O)c(F)c1] | 4-(3-(ethyl(3-(4-methoxyphenyl)propyl)amino)propyl)-2-fluoroprophenol |
| 22 | 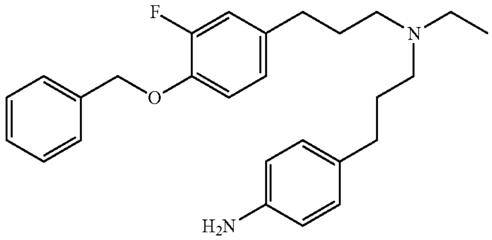 [SMILES: CCN(CCCc1ccc(N)cc1)CCCc1ccc(OCc2ccccc2)c(F)c1] | 4-(3-((3-(4-(benzyloxy)-3-fluorophenyl)propyl)(ethyl)amino) propyl)aniline |
| 23 | 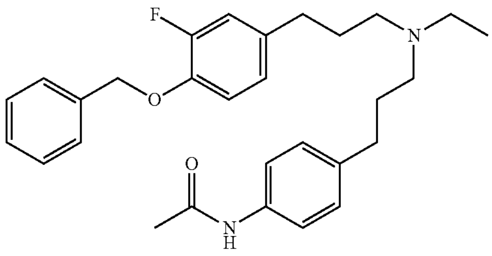 [SMILES: CCN(CCCc1ccc(NC(C)=O)cc1)CCCc1ccc(OCc2ccccc2)c(F)c1] | N-(4-(3-((3-(4-(benzyloxy)-3-fluorophenyl)propyl)(ethyl)amino) propyl)phenyl)acetamide |
| 24 | 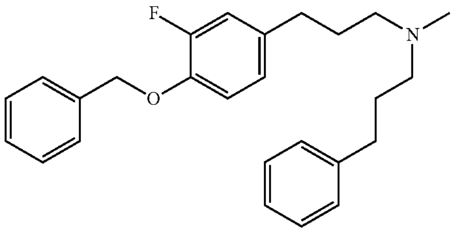 [SMILES: CN(CCCc1ccccc1)CCCc1ccc(OCc2ccccc2)c(F)c1] | 3-(4-(benzyloxy)-3-fluorophenyl)-N-methyl-N-(3-phenylpropyl)propan-1-amine |

TABLE 2-continued

| Derivative name | Structural formula | IUPAC Name |
| --- | --- | --- |
| 25 | 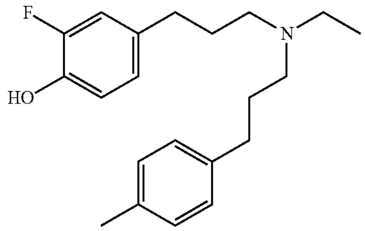 [SMILES: CCN(CCCc1ccc(C)cc1)CCCc1ccc(O)c(F)c1] | 4-(3-(ethyl(3-(p-toly)propyl)amino) propyl)-2-fluorophenol |
| 26 | 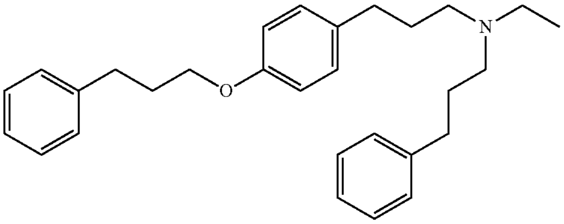 [SMILES: CCN(CCCc1ccccc1)CCCc1ccc(OCCCc2ccccc2)cc1] | N-ethyl-3phenyl-N-(3-(4-(3-phenylpropoxy)phenyl)propyl) propan-1-amine |
| 27 | 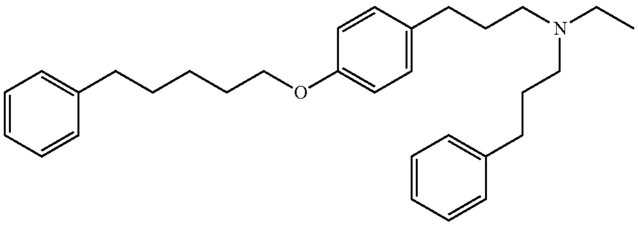 [SMILES: CCN(CCCc1ccccc1)CCCc1ccc(OCCCCCc2ccccc2)cc1] | N-ethyl-3-phenyl-N-(3-(4-((5-phenylpentyl)oxy)phenyl)propyl)propan-1-amine |

In particular, C2C12 cells were dispensed in a 6-well plate treated with the GM of Example 1.1 at a concentration of $5\times10^5$ cells per plate and after 24 hours, were replaced with DMEM media supplemented with 5% HS and induced for differentiation. Then, the cells were treated with DMSO, alverine, or 27 types of alverine derivatives at a concentration of 1 μM. After 4 days, after removing the media, the cells were washed with phosphate buffer (lx PBS) and treated with paraformaldehyde (4%) and fixed at room temperature for 15 minutes. Then, after washing three times with phosphate buffer (1×PBS), PBS containing 0.3% triton X-100 was treated with permeabilization buffer and allowed to react at room temperature for 10 minutes.

After washing three times with phosphate buffer (lx PBS), PBST (blocking buffer, PBS containing 0.5% Tween 20) containing 2% bovine serum albumin was administered and allowed to react for 30 minutes to suppress nonspecific binding of antibodies. After washing with phosphate buffer (1×PBS) three times, 100 μL of primary antibodies against MYH3 (SC-20641, Santa Cruz Biotechnology) diluted to 1:500 were added and allowed to react at room temperature for 1 hour. Thereafter, after washing with phosphate buffer (1×PBS) three times, 100 μL of secondary antibodies (Goat anti-Rabbit IgG-HRP) diluted to 1:5,000 were added and allowed to react at room temperature for 1 hour. After 1 hour, for nuclear staining, after washing with phosphate buffer (1×PBS) three times, the blocking buffer was treated with diluted DAPI dye and allowed to react at room temperature for 10 minutes. Thereafter, after washing with phosphate buffer (1×PBS) three times, the washed cover glass was measured for absorbance at a wavelength of 450 nm and a fluorescent image was taken using a fluorescence microscope.

As a result, it was confirmed that compared with the myoblasts treated with DMSO alone, the myoblasts treated with each of the 27 types of alverine derivatives also all promoted the differentiation to myotubes, just like the myoblasts treated with alverine.

The invention claimed is:

1. A compound selected from the group consisting of:

1) 4-(3-ethyl(3-phenylpropyl)amino)propyl)aniline;

2) N-ethyl-3-(4-methoxyphenyl)-N-(3-phenylpropyl)propan-1-amine;

3) N-ethyl-3-phenyl-N-(3-(p-tolyl)propyl)propan-1-amine;

4) 3-(3-(ethyl(3-phenylpropyl)amino)propyl)phenol;

5) 4-(3-(methyl(3-phenylpropyl)amino)propyl)phenol;

6) 4-(3-((3-(4-(benzyloxy)phenyl)propyl)(ethyl)amino)propyl)aniline;

7) N-(4-(3-((3-)4-(benzyloxy)phenyl)propyl)(ethyl)amino)propyl)phenyl)acetamide;

8) 4-(3-(ethyl(phenethyl)amino)propyl)phenol;

9) 4-(3-(ethyl(3-phenylpropyl)amino)propyl)-2-fluorophenol;

10) 2-bromo-4-(3-(ethyl(3-phenylpropyl)amino)propyl)phenol;

11) 1-(4-(3-((3-(4-(benzyloxy)phenyl)propyl)(ethyl)amino)propyl)phenyl)-3-phenylurea;

12) (4-phenylbutyl)(3-phenylpropyl)propylamine;

13) 3-(4-butoxyphenyl)-N-ethyl-N-(3-phenylpropyl)propan-1-amine;

14) 3-(4-(but-3-en-1-yloxy)phenyl)-N-ethyl-N-(3-phenylpropyl)propan-1-amine;

15) 3-(4-(4-bromobutoxy)phenyl)-N-ethyl-N-(3-phenylpropyl)propan-1-amine;

16) 4-(4-(3-(ethyl(3-phenylpropyl)amino)propyl)phenoxy)butan-1-amine;

17) 4-(3-(ethyl(3-(4-methoxyphenyl)propyl)amino)propyl)-2-fluorophenol;
18) 4-(3-((3-(4-(benzyloxy)-3-fluorophenyl)propyl)(ethyl)amino)propyl)aniline;
19) N-(4-(3-((3-(4-(benzyloxy)-3-fluorophenyl)propyl)(ethyl)amino)propyl)phenyl)acetamide;
20) 3-(4-(benzyloxy)-3-fluorophenyl)-N-methyl-N-(3-phenylpropyl)propan-1-amine;
21) 4-(3-(ethyl(3-(p-tolyl)propyl)amino)propyl)-2-fluorophenol;
22) N-ethyl-3-phenyl-N-(3-(4-(3-phenylpropoxy)phenyl)propyl)propan-1-amine; and
23) N-ethyl-3-phenyl-N-(3-(4-((5-phenylpentyl)oxy)phenyl)propyl)propan-1-amine; or a salt thereof.

2. A method of promoting myoblast differentiation or producing myotubes, comprising treating myoblasts ex vivo with the compound or the salt thereof according to claim 1.

3. A method selected from the following (i)-(iii):

(i) alleviating, or treating a muscle weakness-related condition in a subject in need thereof,
(ii) enhancing muscle strength in a subject in need thereof; or
(iii) a combination of (i) and (ii), said method comprising administering to the subject an effective amount of a compound selected from the group consisting of:

1) 4-(3-ethyl(3-phenylpropyl)amino)propyl)aniline;
2) N-ethyl-3-(4-methoxyphenyl)-N-(3-phenylpropyl)propan-1-amine;
3) N-ethyl-3-phenyl-N-(3-(p-tolyl)propyl)propan-1-amine;
4) 3-(3-(ethyl(3-phenylpropyl)amino)propyl)phenol;
5) N-methyl-3-phenyl-N-(3-phenylpropyl)propan-1-amine;
6) 4,4'-((ethylazanediyl))bis(propan-3,1-diyl))diphenol;
7) 4-(3-(methyl(3-phenylpropyl)amino)propyl)phenol;
8) 4-(3-((3-(4-(benzyloxy)phenyl)propyl)(ethyl)amino)propyl)aniline;
9) N-(4-(3-((3-)4-(benzyloxy)phenyl)propyl)(ethyl)amino)propyl)phenyl)acetamide;
10) 4-(3-(ethyl(phenethyl)amino)propyl)phenol;
11) 4-(3-(ethyl(3-phenylpropyl)amino)propyl)-2-fluorophenol;
12) 2-bromo-4-(3-(ethyl(3-phenylpropyl)amino)propyl)phenol;
13) 1-(4-(3-((3-(4-(benzyloxy)phenyl)propyl)(ethyl)amino)propyl)phenyl)-3-phenylurea;
14) ethyl(4-phenylbutyl)(3-phenylpropyl)amine;
15) ethyl bis(4-phenylbutyl)amine;
16) (4-phenylbutyl)(3-phenylpropyl)propylamine;
17) 3-(4-butoxyphenyl)-N-ethyl-N-(3-phenylpropyl)propan-1-amine;
18) 3-(4-(but-3-en-1-yloxy)phenyl)-N-ethyl-N-(3-phenylpropyl)propan-1-amine;
19) 3-(4-(4-bromobutoxy)phenyl)-N-ethyl-N-(3-phenylpropyl)propan-1-amine;
20) 4-(4-(3-(ethyl(3-phenylpropyl)amino)propyl)phenoxy)butan-1-amine;
21) 4-(3-(ethyl(3-(4-methoxyphenyl)propyl)amino)propyl)-2-fluorophenol;
22) 4-(3-((3-(4-(benzyloxy)-3-fluorophenyl)propyl)(ethyl)amino)propyl)aniline;
23) N-(4-(3-((3-(4-(benzyloxy)-3-fluorophenyl)propyl)(ethyl)amino)propyl)phenyl)acetamide;
24) 3-(4-(benzyloxy)-3-fluorophenyl)-N-methyl-N-(3-phenylpropyl)propan-1-amine;
25) 4-(3-(ethyl(3-(p-tolyl)propyl)amino)propyl)-2-fluorophenol;
26) N-ethyl-3-phenyl-N-(3-(4-(3-phenylpropoxy)phenyl)propyl)propan-1-amine;
27) N-ethyl-3-phenyl-N-(3-(4-((5-phenylpentyl)oxy)phenyl)propyl)propan-1-amine;
28) N-ethyl-3-phenyl-N-(3-phenylpropyl)propan-1-amine; and
29) 4-[3-[ethyl(3-phenylpropyl)amino]propyl]phenol, or a salt thereof.

4. A composition comprising the compound or the salt thereof according to claim 1.

5. The method of claim 3, wherein the muscle weakness-related condition is sarcopenia, muscular atrophy, muscular dystrophy, or cachexia.

6. The composition of claim 4, wherein the salt is a citrate.

7. The composition of claim 4, wherein the composition is a pharmaceutical composition and the composition further comprises a pharmaceutically acceptable carrier.

8. The composition of claim 4, wherein the composition is a food composition and the composition further comprises a sitologically acceptable carrier.

* * * * *